United States Patent
Siniaguine

(10) Patent No.: US 8,237,009 B2
(45) Date of Patent: Aug. 7, 2012

(54) CUSTOM PATTERNED WOUND DRESSINGS HAVING PATTERNED FLUID FLOW BARRIERS AND METHODS OF MANUFACTURING AND USING SAME

(75) Inventor: Oleg Siniaguine, San Carlos, CA (US)

(73) Assignee: PolyRemedy, Inc., San Jose, CA (US)

( * ) Notice: Subject to any disclaimer, the term of this patent is extended or adjusted under 35 U.S.C. 154(b) by 866 days.

(21) Appl. No.: 12/164,451

(22) Filed: Jun. 30, 2008

(65) Prior Publication Data

US 2009/0326429 A1  Dec. 31, 2009

(51) Int. Cl.
*A61F 13/00* (2006.01)
*A61B 17/06* (2006.01)

(52) U.S. Cl. .............. 602/43; 602/41; 602/42; 206/440; 206/441

(58) Field of Classification Search ............... 602/41–59
See application file for complete search history.

(56) References Cited

U.S. PATENT DOCUMENTS

| | | |
|---|---|---|
| 2,682,873 A | 7/1954 | Idnis |
| 2,836,178 A | 5/1958 | Barr |
| 3,140,572 A | 7/1964 | Petersen et al. |
| 3,425,412 A | 2/1969 | Pope |
| 3,729,892 A | 5/1973 | Aslund et al. |
| 3,811,445 A | 5/1974 | Dostal |
| 4,347,841 A | 9/1982 | Benyo et al. |
| 4,522,203 A | 6/1985 | Mays |
| 4,630,426 A | 12/1986 | Gentry |
| 4,751,133 A | 6/1988 | Szycher et al. |
| 4,869,936 A | 9/1989 | Moskowitz et al. |
| 4,917,688 A | 4/1990 | Nelson et al. |
| 4,948,540 A | 8/1990 | Nigam |
| 4,957,795 A | 9/1990 | Reidel et al. |
| 5,000,172 A | 3/1991 | Ward |
| 5,265,605 A | 11/1993 | Afflerbach |
| 5,340,363 A | 8/1994 | Fabo |
| 5,395,305 A | 3/1995 | Koide et al. |
| 5,489,437 A | 2/1996 | Marra |
| 5,520,735 A | 5/1996 | Mulder |
| 5,520,762 A | 5/1996 | Rasmussen et al. |
| 5,588,428 A | 12/1996 | Smith et al. |

(Continued)

FOREIGN PATENT DOCUMENTS

EP  0509703 B1  10/1992

(Continued)

OTHER PUBLICATIONS

European Extended Search Report, European Application No. 05773145.7, Jan. 4, 2011, 10 pages.

(Continued)

*Primary Examiner* — Kim M Lewis
(74) *Attorney, Agent, or Firm* — Fenwick & West LLP

(57) ABSTRACT

A custom fabricated (e.g. custom shaped and dimensioned) wound dressing that matches a corresponding, pre-mapped integumentary wound includes one or more liquid flow barriers composed for example of a hydrophobic and high viscosity liquid embedded in a layer of the dressing. One such embedded hydrophobic liquid barrier covers a skin section immediately adjacent to the wound opening so as to protect the skin section from harmful liquids such as exudates or water. In one embodiment, the skin protecting barrier is substantially comprised of a silicone oil having a viscosity in the range of about 100 cSt to 1000 cSt.

37 Claims, 6 Drawing Sheets

U.S. PATENT DOCUMENTS

| | | | |
|---|---|---|---|
| 5,641,501 A | 6/1997 | Cooper et al. | |
| 5,653,699 A | 8/1997 | Reed et al. | |
| 5,681,579 A | 10/1997 | Freeman | |
| 5,741,509 A * | 4/1998 | Kushner | 424/443 |
| 5,757,498 A | 5/1998 | Klein, II et al. | |
| 5,762,620 A | 6/1998 | Cartmell et al. | |
| 5,785,697 A | 7/1998 | Trombetta et al. | |
| 5,891,078 A | 4/1999 | Turngren et al. | |
| 5,899,871 A | 5/1999 | Cartmell et al. | |
| 5,935,363 A | 8/1999 | Gilman et al. | |
| 6,004,253 A | 12/1999 | Riedel et al. | |
| 6,043,408 A | 3/2000 | Geng | |
| 6,051,747 A | 4/2000 | Lindqvist et al. | |
| 6,062,285 A | 5/2000 | Dotta et al. | |
| 6,071,267 A | 6/2000 | Zamierowski | |
| 6,153,215 A | 11/2000 | Samuelsen et al. | |
| 6,245,960 B1 | 6/2001 | Eaton | |
| 6,284,941 B1 | 9/2001 | Cox et al. | |
| 6,297,420 B1 | 10/2001 | Heincke | |
| 6,313,369 B1 | 11/2001 | Schiraldi et al. | |
| 6,420,622 B1 | 7/2002 | Johnston et al. | |
| 6,512,160 B1 | 1/2003 | Rutsky | |
| 6,520,425 B1 | 2/2003 | Reneker | |
| 6,552,244 B1 * | 4/2003 | Jacques et al. | 602/43 |
| 6,655,112 B1 | 12/2003 | Cremer et al. | |
| 6,662,051 B1 | 12/2003 | Eraker et al. | |
| 6,753,454 B1 | 6/2004 | Smith et al. | |
| 6,765,123 B2 | 7/2004 | de Jong et al. | |
| 6,787,682 B2 | 9/2004 | Gilman | |
| 6,967,261 B1 | 11/2005 | Soerens et al. | |
| 7,105,058 B1 | 9/2006 | Sinyagin | |
| 7,347,846 B2 | 3/2008 | Hermansson et al. | |
| 2001/0000795 A1 | 5/2001 | Bolian, II et al. | |
| 2001/0003148 A1 | 6/2001 | Coffee | |
| 2002/0062097 A1 | 5/2002 | Simpson | |
| 2002/0133502 A1 | 9/2002 | Rosenthal et al. | |
| 2003/0050794 A1 | 3/2003 | Keck | |
| 2003/0233101 A1 | 12/2003 | Lubock et al. | |
| 2004/0015115 A1 * | 1/2004 | Sinyagin | 602/42 |
| 2004/0059199 A1 | 3/2004 | Thomas et al. | |
| 2004/0133143 A1 | 7/2004 | Burton et al. | |
| 2004/0167456 A1 | 8/2004 | Kingsford et al. | |
| 2005/0149259 A1 | 7/2005 | Cherveny et al. | |
| 2005/0182347 A1 * | 8/2005 | Bishop et al. | 602/43 |
| 2006/0020235 A1 | 1/2006 | Siniaguine | |
| 2006/0034816 A1 | 2/2006 | Davis et al. | |
| 2007/0118096 A1 | 5/2007 | Smith et al. | |
| 2007/0204691 A1 | 9/2007 | Bogner et al. | |
| 2007/0207688 A1 | 9/2007 | Rasor | |
| 2007/0237812 A1 | 10/2007 | Patel et al. | |
| 2008/0004904 A1 | 1/2008 | Tran | |
| 2008/0051688 A1 | 2/2008 | Lowe | |
| 2008/0077091 A1 | 3/2008 | Mulligan | |
| 2008/0108923 A1 | 5/2008 | Sinyagin | |
| 2008/0108927 A1 | 5/2008 | Sinyagin | |
| 2008/0167594 A1 | 7/2008 | Siniaguine | |
| 2008/0234618 A1 | 9/2008 | Baldock | |
| 2009/0024067 A1 | 1/2009 | Siniaguine | |
| 2009/0037224 A1 | 2/2009 | Raduchel | |
| 2009/0131825 A1 | 5/2009 | Burbank et al. | |
| 2009/0204423 A1 | 8/2009 | DeGheest et al. | |
| 2009/0216553 A1 | 8/2009 | Cellura | |
| 2009/0245603 A1 | 10/2009 | Koruga et al. | |
| 2010/0114256 A1 | 5/2010 | Chan et al. | |
| 2010/0219546 A1 | 9/2010 | Puttler et al. | |

FOREIGN PATENT DOCUMENTS

| | | |
|---|---|---|
| WO | WO 97/42917 A1 | 11/1997 |
| WO | WO 00/43046 A2 | 7/2000 |

OTHER PUBLICATIONS

European Examination Report, European Application No. 03728787.7, Nov. 15, 2010, 6 pages.
United States Office Action, U.S. Appl. No. 12/110,228, Oct. 22, 2010, 21 pages.
United States Office Action, U.S. Appl. No. 12/436,071, Oct. 22, 2010, 18 pages.
United States Office Action, U.S. Appl. No. 11/972,452, Dec. 3, 2010, 9 pages.
United States Office Action, U.S. Appl. No. 12/198,676, Jan. 19, 2011, 8 pages.
United States Office Action, U.S. Appl. No. 10/431,888, Jun. 10, 2010, 18 pages.
European Search Report, EP 03 72 8787.7, dated May 24, 2006, 4 pages.
Examination Report of the European Patent Office, EP 03 72 8787.7, dated May 18, 2007, 7 pages.
International Search Report, PCT/US03/14574, mailing date Oct. 1, 2003.
PCT International Search Report and Written Opinion, PCT/US2009/048412, Oct. 13, 2009, 13 pages.
PCT International Search Report and Written Opinion, PCT/US2008/50762. Jun. 25, 2008, 10 pages.
PCT International Search Report and Written Opinion, PCT/US2005/25362, Sep. 1, 2006, 9 pages.
Siniaguine, O., "Automatic System for On-Demand Fabrication of Wound Dressings," 2007, pp. 1-15.
United States Office Action, U.S. Appl. No. 10/431,888, Aug. 17, 2009, 17 pages.
United States Office Action, U.S. Appl. No. 10/431,888, Jun. 23, 2009, 14 pages.
United States Office Action, U.S. Appl. No. 10/431,888, Nov. 25, 2008, 11 pages.
United States Office Action, U.S. Appl. No. 10/431,888, Dec. 11, 2007, 8 pages.
United States Office Action, U.S. Appl. No. 10/431,888, Apr. 10, 2007, 7 pages.
United States Office Action, U.S. Appl. No. 11/972,854, Feb. 2, 2010 14 pages.
United States Office Action, U.S. Appl. No. 11/972,854, Jun. 24, 2009, 8 pages.
United States Office Action, U.S. Appl. No. 11/972,846, Jan. 25, 2010, 12 pages.
United States Office Action, U.S. Appl. No. 11/972,846, Jun. 24, 2009, 8 pages.
United States Office Action, U.S. Appl. No. 12/198,604, Jan. 21, 2010, 30 pages.
United States Office Action, U.S. Appl. No. 12/198,604, Jun. 25, 2009, 12 pages.
United States Office Action, U.S. Appl. No. 12/198,676, Sep. 16, 2009, 8 pages.
United States Office Action, U.S. Appl. No. 11/183,459, May 9, 2008, 9 pages.
United States Office Action, U.S. Appl. No. 10/382,422, May 2, 2005, 16 pages.
U.S. Appl. No. 10/431,058.
U.S. Appl. No. 12/196,908, filed Aug. 22, 2008, Siniaguine.
U.S. Appl. No. 11/183,459, filed Jul. 8, 2005, Siniaguine.
U.S. Appl. No. 12/436,071, filed May 5, 2009, Siniaguine.
"IMPAC Introduces Comprehensive Cancer Outcomes Analytical Suites," Business Wire, published Mar. 7, 2000. Dialog, (File 610 Business Wire), Dialog ID No. 00210331.
"Iteration" Wikipedia, 3 pages, [Online] [Retrieved on Feb. 28, 2011] Retrieved from the Internet<URL:www.wikipedia.com>.
United States Office Action, U.S. Appl. No. 12/110,228, Mar. 7, 2011, 21 pages.
United States Office Action, U.S. Appl. No. 12/436,071, Apr. 1, 2011, 20 pages.
Canadian Examination Report, Canadian Application No. 2,524,934, Feb. 8, 2010, 3 pages.
European Examination Report, European Application No. 03728787.7, Feb. 26, 2010, 4 pages.
International Search Report and Written Opinion, PCT/US2009/054458, Oct. 9, 2009, 3 pages.
United States Office Action, U.S. Appl. No. 12/198,676, Mar. 12, 2010, 7 pages.
U.S. Appl. No. 10/431,888, filed May 7, 2003, Sinyagin.
U.S. Appl. No. 11/972,854, filed Jan. 11, 2008, Sinyagin.
U.S. Appl. No. 11/972,846, filed Jan. 11, 2008, Sinyagin.
U.S. Appl. No. 10/382,422, filed Mar. 5, 2003, Sinyagin.

U.S. Appl. No. 11/972,452, filed Jan. 10, 2008, Siniaguine.
U.S. Appl. No. 12/110,228, filed Apr. 25, 2008, DeGheest et al.
U.S. Appl. No. 12/436,071, filed May 5, 2009, Siniaguine et al.
United States Office Action, U.S. Appl. No. 11/972,452, Jun. 14, 2011, 7 pages.
United States Office Action, U.S. Appl. No. 12/198,676, May 13, 2011, 8 pages.
PCT International Search Report and Written Opinion, PCT/US2010/031912, Jun. 18, 2010, 13 pages.
U.S. Appl. No. 12/198,604, filed Aug. 26, 2008, Oleg Siniaguine.
U.S. Appl. No. 12/198,676, filed Aug. 26, 2008, Oleg Siniaguine.
International Search Report, PCT/US09/039545, mailing date May 29, 2009.
Written Opinion of the International Searching Authority, PCT/US09/039545.
United States Office Action, U.S. Appl. No. 12/110,228, Jul. 28, 2011, 21 pages.
United States Office Action, U.S. Appl. No. 11/972,452, Jul. 28, 2011, 6 pages.
United States Office Action, U.S. Appl. No. 12/436,071, Aug. 24, 2011, 19 pages.
United States Office Action, U.S. Appl. No. 12/198,676, Sep. 6, 2011, 8 pages.
U.S. Appl. No. 60/840,412, filed Aug. 28, 2006, Lowe, 6 pages.
European Examination Report, European Application No. 05773145.7, Jan. 17, 2012, 5 pages.
United States Office Action, U.S. Appl. No. 11/972,452, Nov. 10, 2011, 6 pages.
United States Office Action, U.S. Appl. No. 12/196,908, Sep. 30, 2011, 7 pages.
United States Office Action, U.S. Appl. No. 12/110,228, Jan. 31, 2012, 20 pages.
United States Office Action, U.S. Appl. No. 12/436,071, Feb. 13, 2012, 18 pages.
United States Office Action, U.S. Appl. No. 13/052,553, Mar. 20, 2012, 9 pages.

* cited by examiner

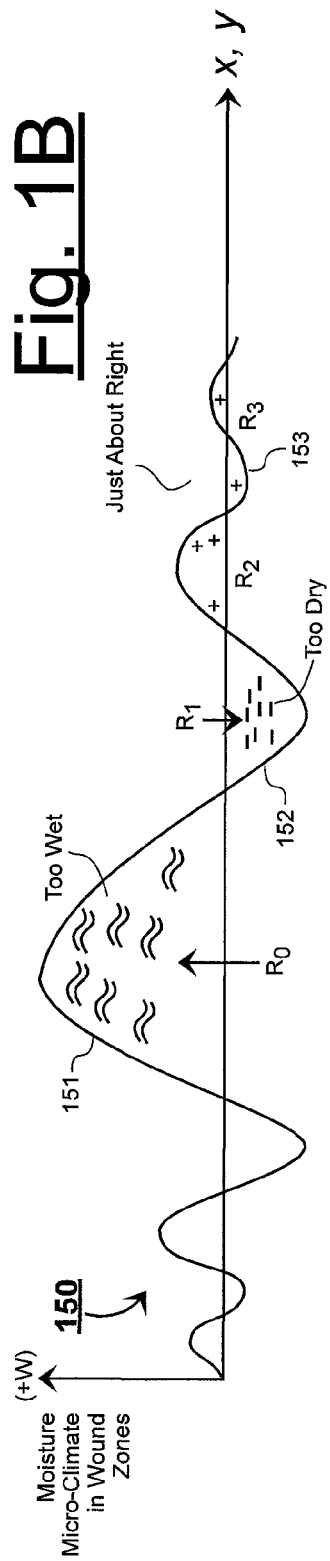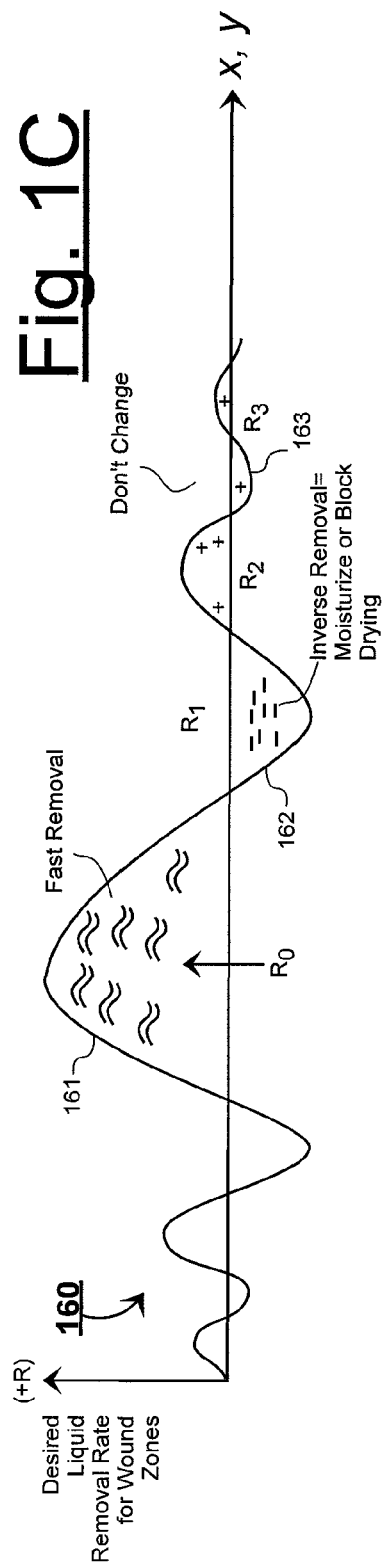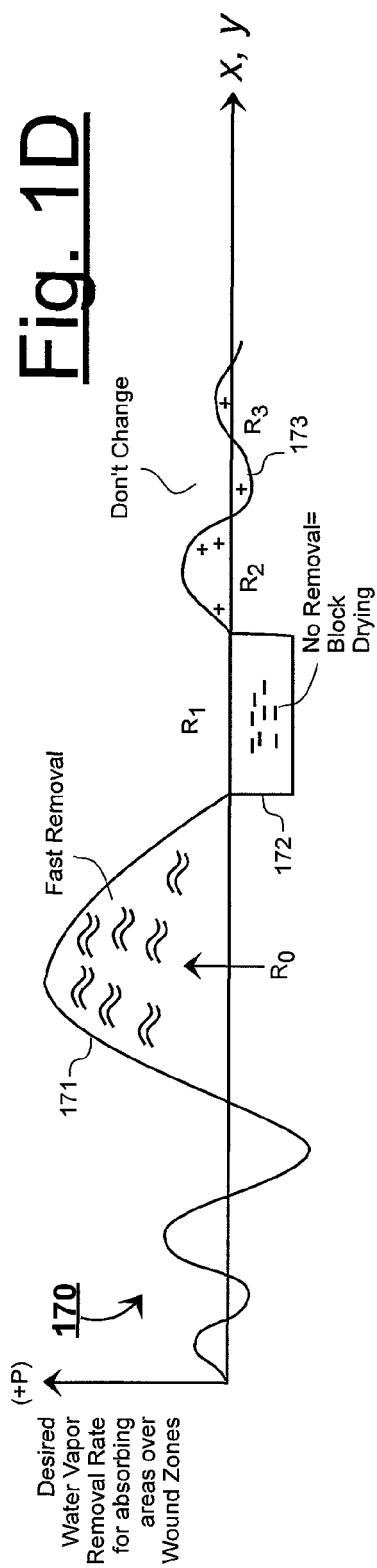

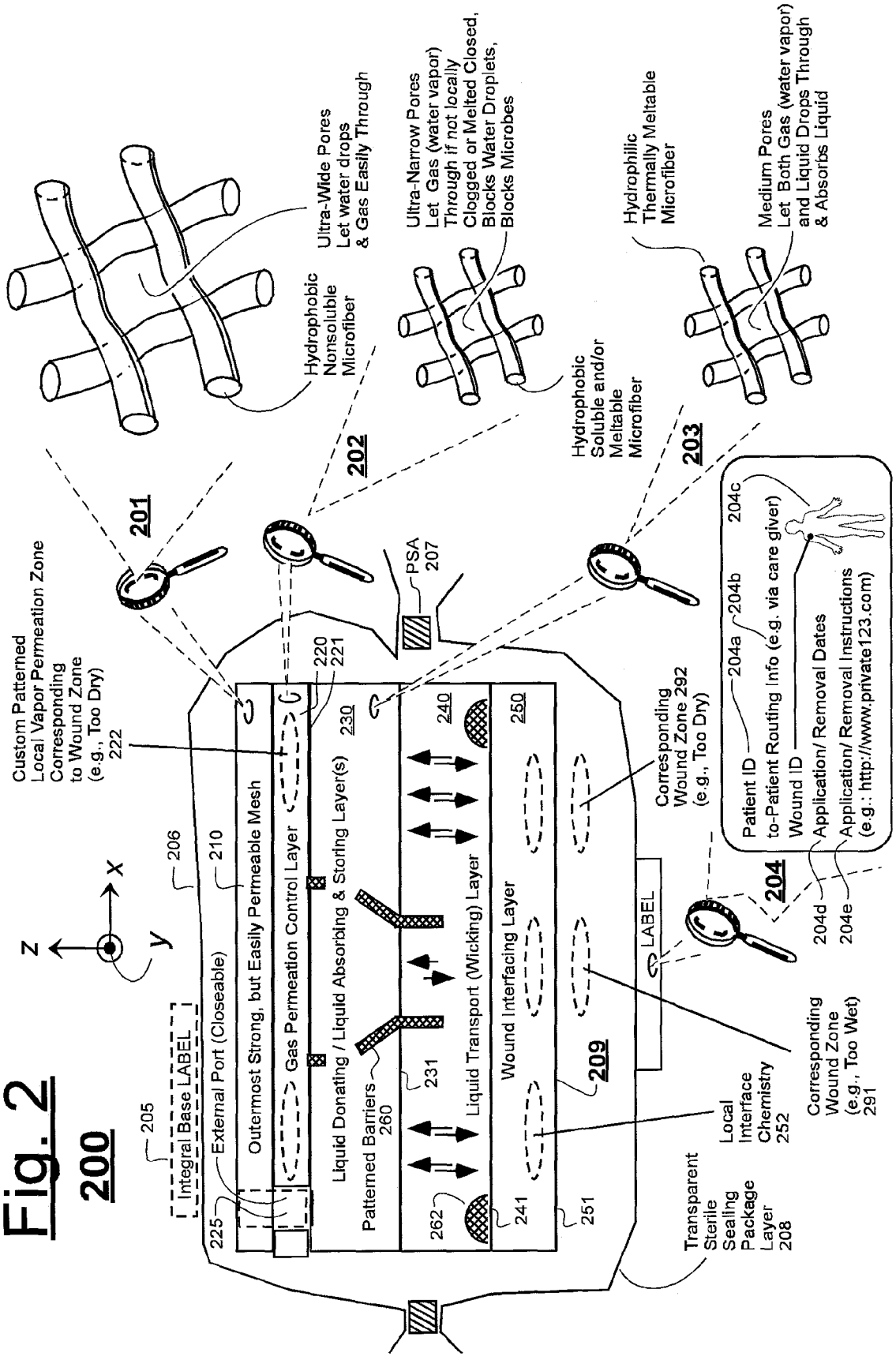

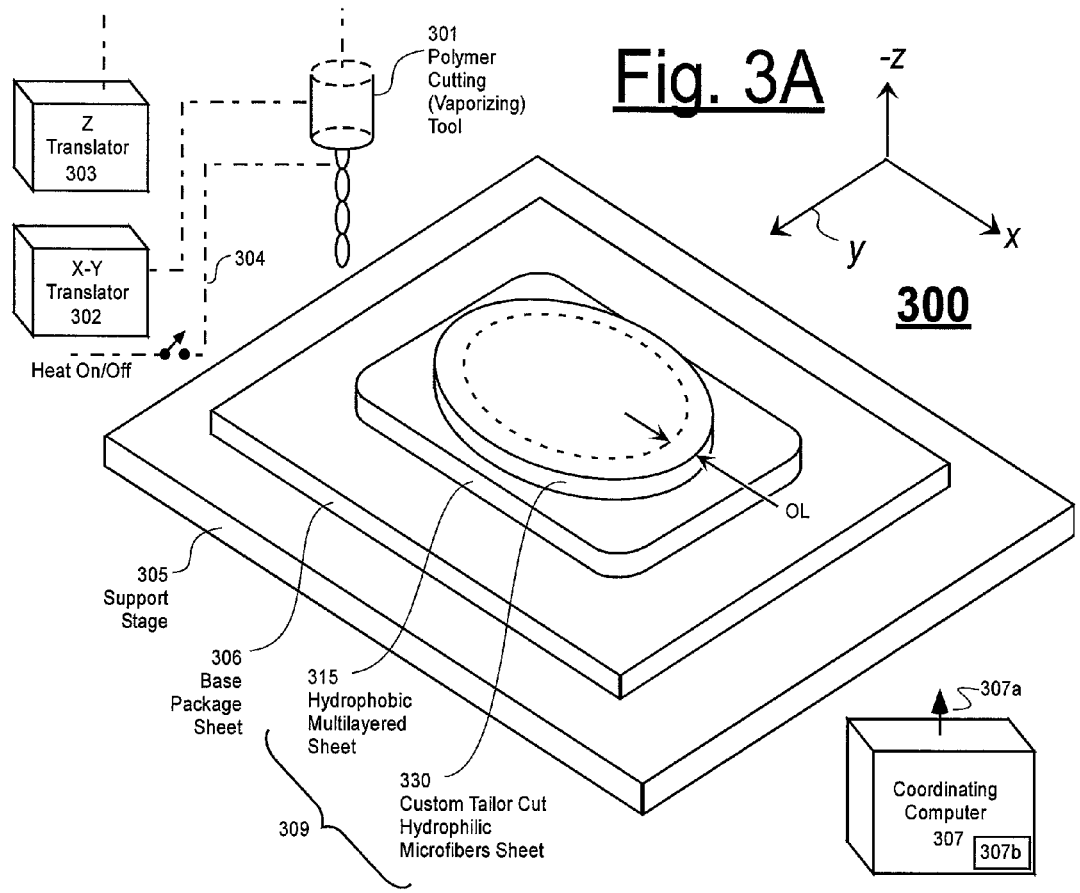
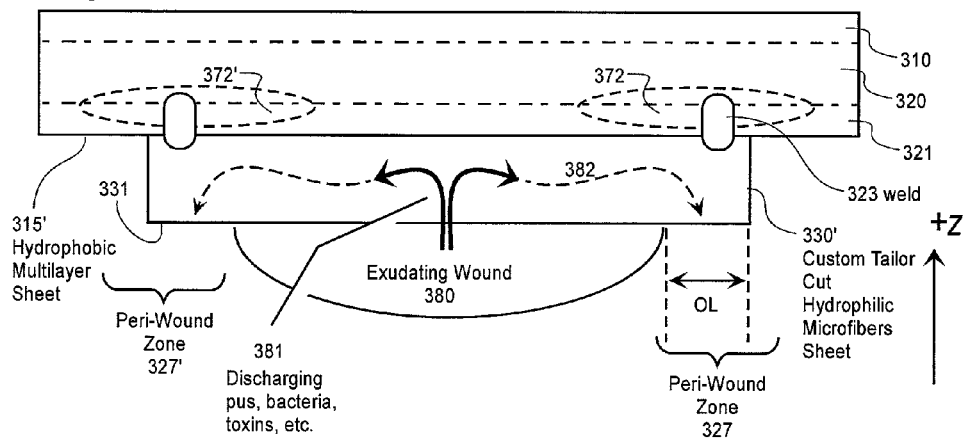

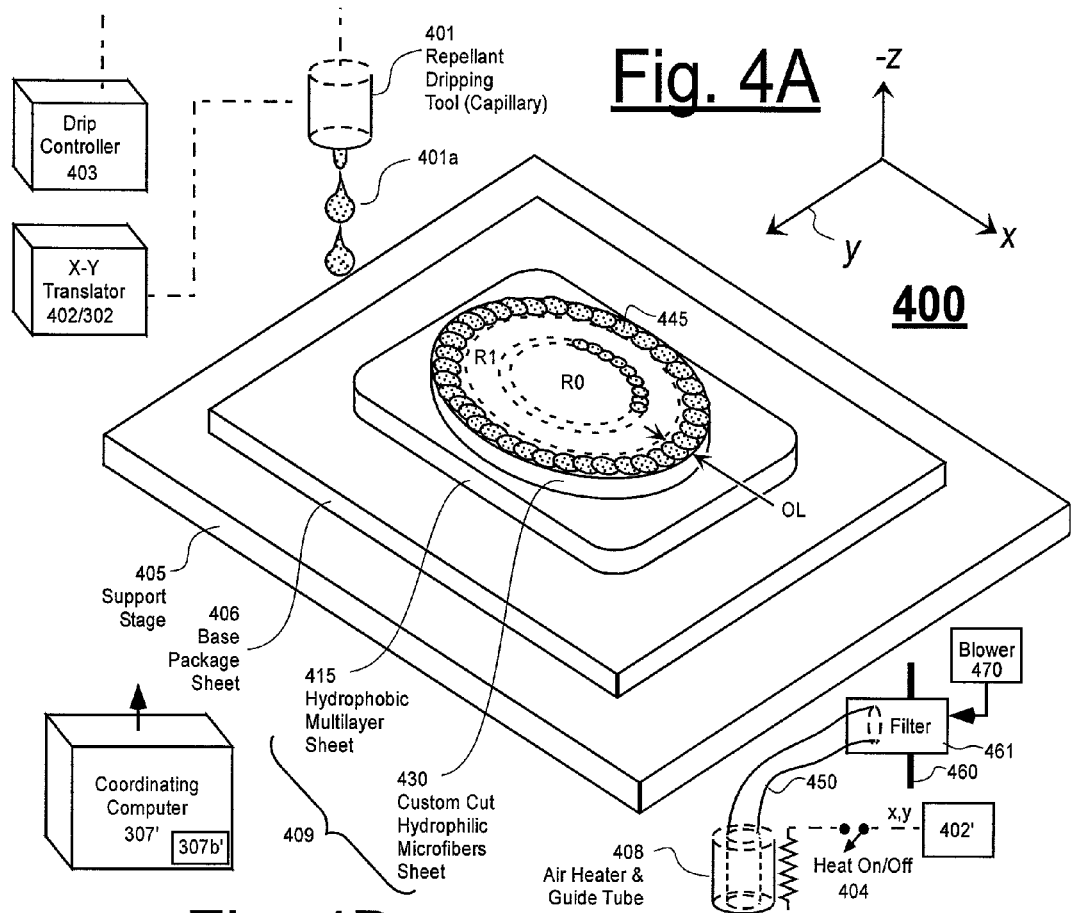

CUSTOM PATTERNED WOUND DRESSINGS HAVING PATTERNED FLUID FLOW BARRIERS AND METHODS OF MANUFACTURING AND USING SAME

CROSS REFERENCE TO AND INCORPORATION OF CO-OWNED APPLICATION

The following copending U.S. patent application is owned by the owner of the present application, and its disclosure is incorporated herein by reference:

(A) U.S. Ser. No. 11/972,452 filed Jan. 10, 2008 by Oleg SINIAGUINE, originally entitled, "Wound Dressing with Controllable Permeability", and claiming priority of and incorporating U.S. Provisional applications 60/884,321 filed Jan. 10, 2007 and 60/888,693 filed Feb. 7, 2007.

CROSS REFERENCE TO AND INCORPORATION OF PUBLISHED APPLICATIONS AND PATENTS

The disclosures of the following published U.S. patent applications or patents are incorporated herein by reference:

(A) U.S. Pat. No. 7,105,058, issued Sep. 12, 2006 to Dmitriy Sinyagin and entitled "Apparatus for Forming Microfiber Coating";

(B) U.S. Pat. Publication No. 2004-0015115 and its underlying source: U.S. Ser. No. 10/431,888 filed May 7, 2003 by Dmitriy Sinyagin, originally entitled, "Method for Treating Wound, Dressing for Use Therewith, and Apparatus and System for Fabricating Dressing", and claiming priority of and incorporating U.S. Provisional application 60/378,635 filed May 7, 2002; and (C) U.S. Pat. Publication No. 2006-0020235 and its underlying source: U.S. Ser. No. 11/183,459 filed Jul. 18, 2005 by Oleg Siniaguine, originally entitled, "Wound Dressing and Apparatus for Manufacturing", and claiming priority of and incorporating U.S. Provisional application 60/588,628 filed Jul. 16, 2004.

FIELD OF DISCLOSURE

The present disclosure of invention relates generally to care and management of wounds to the integumentary systems of humans or other mammals. The disclosure relates more specifically to the fabrication and use of custom tailored wound dressings that are custom patterned to match individual needs of individual wound zones over time on individual patients.

DESCRIPTION OF RELATED TECHNOLOGY

The outer protective system or integument of human and other mammalian bodies is a complex system that is typically comprised of growing, aging and dying or dead skin cells; of oil glands, sweat glands, hair and hair follicles, peripheral blood vessels (capillaries), nerve endings and other components. For land dwelling mammals, the integument serves as a protective interface between delicate internal organs and a generally dry, and often microbe populated (dirty) and abrasive ambient environment which is hostile to delicate internal organs that need to be kept moisturized, fed with oxygenated blood, kept free of harmful microorganisms and kept at healthy body temperatures.

Healthy skin is constantly generating new skin cells (epitheliating cells) and progressively converting these new skin cells into aging, drying and dying cells that push their way outwardly through the epidermis to interface with the generally dry, dirty and abrasive ambient environment. Aside from interfacing with the generally hostile external environment, healthy skin generally performs many other vital functions including that of regulating body temperature (e.g., by sweating), excreting waste products (e.g., salts) and providing sense of touch.

In order to continue to provide these various functions, different levels of the epidermis in the skin require correspondingly different ones of graduated micro-climates and different physiochemical micro-environments. These graduated and differentiated micro-environments range from that of a relatively dry, yet nonetheless oil lubricated one at the outer surface of the epidermis to a relatively wet, fluidic and flowing environment at deeper levels of the integument where the basal epidermis and deeper parts of the integument tend to be populated by blood vessels and growing, dividing cells and the like.

When a skin puncturing wound occurs, these graduated systems of differentiated micro-climates and physiochemical micro-environments are disrupted. Areas of skin that are normally relatively dry may become unduly wet due to flow of liquids (exudates) that discharge from the wound center and move out uncontrollably over drier skin areas. On the other hand, deeper parts of the skin structure that are normally wet and free of harmful microorganisms may become unduly dry and infected with colonized bacteria due to exposure to open air and contaminants.

Conventional wound treatments apply a homogenous wound dressing (e.g., one made of woven cotton threads) over the entire wound area primarily for the purpose of keeping the wound clean, protecting it from external contaminants as well as direct physical trauma and perhaps soaking up some initial bleeding.

More recently, custom tailored wound dressings have been proposed for treating wounds individually and at different stages of their development. More specifically, individual wounds of individual patients are mapped, measured and characterized according to their localized zones. For example, digital images of the wounds, with size calibration are taken in a natural visible light range and/or by other means (e.g., polarized light, IR images, UV images, etc.) and by associating different identifiable areas of the imaged wound with different wound zone characteristics (e.g., overly wet zone, overly dry zone, etc.). Individual or overlapping treatment goals are then assigned to each of differently characterized wound zones. Thereafter corresponding dressing functions are designated for each of the differently characterized wound zones and these dressing functions (e.g., heavy absorption of moisture, blocking of evaporation, etc.) are unified to define a custom tailored dressing that is automatically fabricated for and according to the individual dimensions of the individual wound zones of a given individual patient. The above-cited U.S. patent applications (incorporated herein by reference) disclose various methods for automatically custom designing and custom fabricating individual dressings for individual wounds.

In forming the custom tailored wound dressings, there is one aspect of wound treatment that is often overlooked, namely, the needs of the surrounding skin.

SUMMARY

Protection and/or nourishment of the skin surrounding an integumentary wound are important because that skin is often the source of wound-closing re-growth. If healthy skin adjacent to an open wound is allowed to degrade or deteriorate due to benign neglect, the skin may begin to contribute in its degraded form to the expansion and worsening of the original wound instead of contributing to contraction and healing of the wound.

In accordance with one aspect of the present disclosure, liquid flow blocking barriers are custom designed and integrated into a custom patterned wound dressing so as to block potentially harmful liquids (e.g., wound exudates) from flowing into contact with skin adjacent to a wound; or so as to reduce the amount of, or length of time that such harmful liquids that are allowed to contact the adjacent skin. The potentially harmful liquids may include aqueous exudates that can carry microbes or corrosive, toxic chemicals. They may also include simple water, where prolonged exposure to the latter can degrade healthy skin.

In accordance with one embodiment, a dividing line, or a constraining ring or another dividing pattern is defined at one or more custom picked locations in a wound dressing by pattern wise depositing a hydrophobic liquid onto a laterally extending layer of the wound dressing. The deposited hydrophobic liquid is caused to infiltrate vertically at least partially into the thickness of the lateral dressing layer and to become embedded therein. Viscosity of the embedded hydrophobic liquid relative to the dressing layer that contains it (in other words, resistance of the embedded liquid to further flowing within the dressing layer) is caused to be (or is from the start) sufficiently high after infiltration so that the embedded hydrophobic liquid substantially resists being further displaced from its initial locus of infiltration within the dressing layer. The embedded hydrophobic liquid substantially comprises or essentially consists of a hydrophobic material (one that repels water and/or repels aqueous solutions such as wound exudates) and it thus functions as a barrier to water or aqueous solutions flowing through it from one side of the barrier to an opposed other side. In one embodiment, the hydrophobic liquid is deposited and infiltrated into a skin contacting layer of a dressing so as to define a customized barrier that blocks or substantially inhibits the flow of water, exudates and/or other liquids that may be potentially harmful to skin from contacting a skin area for a prolonged time where the protected skin area is one contacted by the skin contacting layer. As such, wound-adjacent skin is protected from prolonged contact with water, exudates and/or other potentially harmful liquids and is given a better chance to grow and close up the wound.

More specifically, in one embodiment, one or more silicones (polysiloxanes), silicone oils, and/or non-aqueous organic or inorganic solutions thereof (e.g., a solution including a solvent which temporarily reduces the viscosity of the included silicone(s)) is deposited in the form of a custom tailored pattern on areas of a wound dressing layer that are designated to contact healthy skin or peri-wound skin adjacent to a given, pre-mapped wound. The deposited silicone(s), silicone oil(s), or silicone solution(s) is/are formulated to infiltrate at least partially into, if not entirely through the thickness of the skin contacting layer and to thereafter become more firmly embedded in that wound dressing layer. In other words, the deposited and infiltrated silicone(s)/solution(s) and/or the dressing layer into which it/they are infiltrated, is/are formulated so that the deposited hydrophobic liquid(s) substantially retain its/their deposited pattern or shape after having infiltrated partially or fully into the thickness of the corresponding dressing layer. In one embodiment, the corresponding dressing layer substantially comprises or essentially consists of a nonwoven mesh of organic polymer microfibers with a relatively small average pore size. Once a certain volume of infiltrating hydrophobic liquid becomes enmeshed in the microfiber matrix and its infiltration speed slows, surface tension and/or capillary effects take over to prevent the embedded hydrophobic liquid from spreading substantially farther. The partially or fully infiltrated silicone material then defines a custom-patterned and pattern-retaining barrier that blocks or repels the flow of water and/or aqueous solutions (e.g., exudates) through its area of infiltration.

In one embodiment, the infiltrated silicone(s) has/have a viscosity in the range of 1 cSt to 10,000 cSt (CentiStokes). The specific viscosity or viscosities used depends on the porosity and/or other characteristics of the infiltrated wound dressing layer (e.g., the whettability of microfibers in the wound dressing layer by the utilized silicone or silicones) and on the functions that the deposited silicone(s) are asked to perform. For example, not all of the deposited silicones may be designed to retain their original shape for a long time. Some may be intentionally designed to flow into an adjacent, temporarily moisturized area of the wound dressing after the moisture (e.g., water and/or medicine) has been dissipated from that adjacent, temporarily moisturized area. In one embodiment, a silicone oil is used having a viscosity in the range of 100 cSt to 1,000 cSt, or nominally, a viscosity of about 500 cSt.

Silicone is not the only patternable and water-blocking material that may be used to form a custom patterned barrier. A wide variety of other liquids or gels whose viscosity, fluidity and infiltration into a porous layer may be controlled and that are themselves not generally harmful to skin may be used, including various vegetable oils and mineral oils. Silicones (polysiloxanes) are particularly attractive for this function because their viscosities can be custom tailored to match porosities and other attributes of polymer microfiberous sheets and because silicones are generally not harmful to healthy skin. (Of course, if a given patient is allergic to one or more silicones, other materials would have to be used. Automated recognition of patient allergies and adaptive response thereto can be part of the custom design process for fabricating a custom wound dressing matching a given wound and an individual patient.)

Intrinsic silicones tend to be colorless. However, non-toxic colored dyes may be added to them. See for example U.S. Pat. No. 4,737,537 (Colored Silicone Composition) whose disclosure is incorporated herein by reference. In accordance with one aspect of the present disclosure, silicones or other water repellant barrier liquids are colored by adding thereto non-toxic dyes (e.g., not harmful to skin or other tissue) so as to form readily visible boundary lines or curves on the wound facing surface of a wound dressing. The dye color may be selected to contrast strongly with the color of the wound facing surface of a wound dressing and/or with a medicinal addend that is to be added in a region whose boundary is defined by the water repellant barrier liquid(s). For example if the dressing surface is white, the selected dye color may be a dark blue or green. Users may then be instructed to infuse water, saline solution or specific medications into visibly bounded regions on a custom dressing. The colored water repellant barrier liquids may also be used to label the bounded regions that the repellant barrier liquids define such as marking a first region as "i", a second as "ii" and so forth.

Full circle coordination and control of wound treatment design and of application of a corresponding custom designed wound dressing may be provided by a packaged product formed in accordance with the disclosure under control of a coordinating computer program where the program oversees mapping and characterization of a given wound, automated fabrication of a corresponding wound dressing, and automated packaging of the fabricated dressing into a sterile or clean package having functional routing and/or usage indicia provided thereon for getting the packaged product routed to a correct patient and a matching wound on that patient.

Other aspects of the disclosure will become apparent from the below detailed description.

BRIEF DESCRIPTION OF THE DRAWINGS

The below detailed description section makes reference to the accompanying drawings, in which:

FIG. 1B is a first schematic plot for explaining how various zones in an open wound can be too wet or too dry or otherwise not condition for speedy healing;

FIG. 1C is a second schematic plot for explaining how liquid removal and/or liquid sourcing paradigms can be devised within a custom patterned dressing to match the locations and rates of the too wet and/or too dry wound zones of FIG. 1B;

FIG. 1D is a third schematic plot for explaining how outgas permeation rates (e.g., evaporation rates) can be devised to match the locations and rates of the fast liquid removing and inverse removing dressing zones of FIG. 1C;

FIG. 2 is a schematic diagram illustrating a sterile-wise packaged, custom patterned dressing in accordance with the present disclosure;

FIG. 3A is a perspective view of a first intermediate step in an automated fabrication process where a custom patterned dressing in accordance with the disclosure is being formed and where a hydrophobic double layer has been provided on a base packaging layer, and a first hydrophilic microfiber layer of wound-matching dimensions has been custom cut and deposited thereon;

FIG. 3B is a side sectional view showing how the wound-matching hydrophilic microfiber layer of FIG. 3A is intended to overlay peri-wound and/or healthy skin adjacent the open wound;

FIG. 4A is a perspective view of a second step in an automated fabrication process where a custom patterned dressing in accordance with the disclosure is being formed and fluid blocking barriers of predefined dimensions and shapes are being formed in the first hydrophilic microfiber layer;

FIG. 4B is a side sectional view showing how the wound-matching fluid blocking barriers of FIG. 4A are intended to align with and overlay respective exudating, dry and peri-wound and/or healthy skin regions adjacent the pre-measured and pre-mapped open wound;

DETAILED DESCRIPTION

Figure 1A:
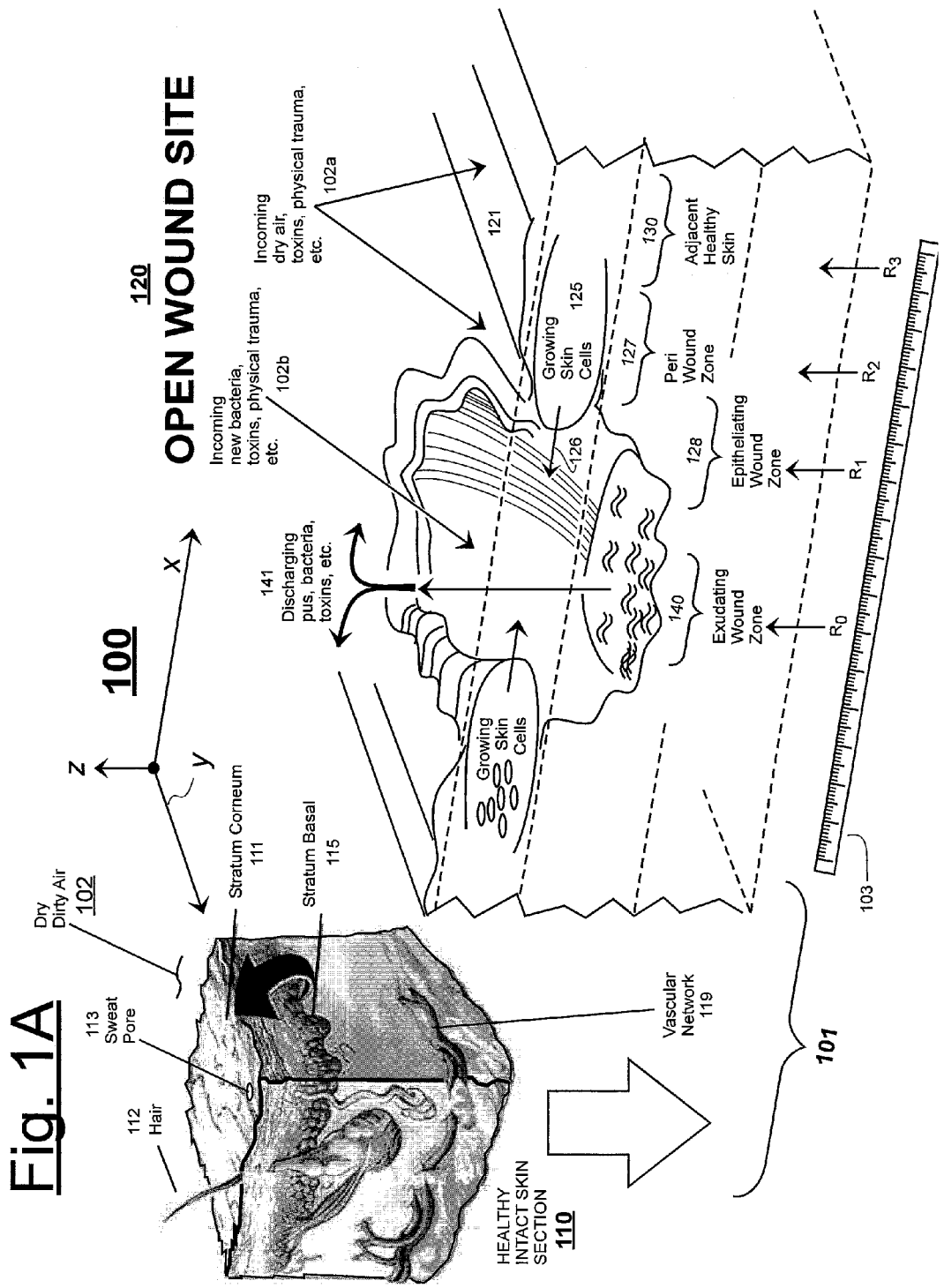
FIG. 1A is a perspective schematic showing a block of healthy intact skin and an adjacent open wound.

FIG. 1A schematically represents a combination 100 of a given human living body 101 interacting with a potentially hostile external environment 102 (e.g., air contaminated with harmful microbes, with dirt, toxins, etc. and other surroundings which can inflict trauma on the body). Portion 110 of the body 101 represents a hypothetically sectionally removed cube of healthy skin tissue lying adjacent to an open wound site 120 also belonging to the given human patient 101. As seen, the healthy section 110 comprises a complex assortment of organelles and layers including a relatively dry and dead top portion 111 (stratum corneum) of the epidermis and a moderately wet, alive and reproducing basal portion 115 (stratum basal) of the epidermis.

Additionally, healthy and intact section 110 includes oil glands, hair follicles, hair 112, sweat pores 113, and a vascular network 119 positioned deeper within section 110. The vascular network 119 supplies oxygen, water and nutrients to the growing and reproducing cells of the basal portion 115 of the epidermis. It may be appreciated from FIG. 1A that the concentration of water in a healthy skin section such as 110 typically decreases as a continuum as one rises in the +Z (vertical) direction from the relatively wet environment of intact vascular network layer 119, through the epithelizing basal layer 115 and up to the aged and dry skin cells at the very top 111 of the epidermis. As is well known in the medical arts, dead skin cells are constantly flaking off in unnoticed quantities from the outermost part 111 of a healthy epidermis as the body 101 interacts abrasively with the outside environment 102 and new cells are constantly being generated by the intact and healthy basal layer 115 to replace the flaked off dermis.

Referring to the perspective schematic of the adjacent open wound site 120 in FIG. 1A, it may be seen that once an open wound is created, the moderately moist, normal environment of the intact basal layer 115 is not present for exposed growing skin cells 125 that are trying to grow radially inward (in direction 126) to close up the wound opening. Instead these inward growth-attempting cells 125 are exposed to a much dryer and otherwise more hostile environment 102a due to the incoming dry air entering through the opening of wound site 120. During normal healing, epitheliating cells 125 grow laterally in a wound closing direction 126 from the still-intact surrounding skin (127 and/or 130) towards the center region, $R_0$ of the wound. At the same time, deeper vascular tissue (e.g., 119) tries to thrive and grow vertically upward in the +Z direction so as to restore the underlying support structure that nourishes the basal portion 115 of the epidermis in healthy intact skin (110). These various activities are desirable in order to close up the wound and permit quick healing.

Of course, many different mechanisms may be present to compete against and/or to block the radially inward healing process 126 attempted by peri-wound tissue (125, 127) and/or to thwart the upwardly moving (+Z) growth and restructuring processes attempted by the deeper tissue of the wound site 120. For example, the patient 101 may be afflicted with chronic diabetes, and/or with an impaired immune system, or old age, and/or other medical conditions that prevent normal rapid healing. Aside from that, the open wound 120 may be exposed to dry and potentially dirty incoming air 102a as already mentioned. Secondly, one or more central regions (e.g., $R_0$) of the wound may have been infected by and thus colonized by harmful bacteria where that bacteria is causing damage to the subdermal tissue and impeding healing re-growth or even expanding the size of the wound due to expansion of the infection. Additionally or alternatively, new bacteria may enter the open wound site 120 from the outside environment 102b and thus infect it. When infections, external trauma or the like occur, the immune system and other aspects of the body try to go to work and to begin generating protective liquids in the process of fighting off invading microbes and/or filling up the open wound cavity. Some of the generated liquids (exudates) may be harmful to surrounding healthy skin (e.g., to areas 121, 125, 127 and 130). Exudating liquids may include discharging pus, growing bacteria, and toxic chemicals generated in the exudating wound zone 140. If the surrounding healthy skin (121, 125, 127, 130) is harmed, it may not be able to contribute to the healing process (126) or worse yet, the exuded liquids may cause the wound site 120 to grow even larger.

Every human patient 101 is different and may have unique wound treatment requirements including that of supplying a clean flow of medications into the wound site. Additionally one patient may have multiple wounds (e.g., sores, ulcers, etc.) of different sizes, shapes and morphologies. Depending on whether certain disease processes are present in different body regions and so forth, each wound site 120 may have a variety of differently characterized zones and each wound zone may have its own individual shape, topography, dimensions and treatment needs. As such, each wound site may have to be treated individually. By way of example, open wound site 120 of FIG. 1A is shown to have a centrally located, heavily exudating zone 140 at position $R_0$, and an overly dry, epitheliating wound zone 128 at first radial position $R_1$. The illustrated wound site 120 is further shown to have a peri-wound zone 127 at second radial position $R_2$, and to have further away from the peri-wound zone 127, an adjacent and intact healthy skin zone 130 at third radial position $R_3$. A topmost skin layer 121 may cover the healthy adjacent skin 130 and may partially cover the peri-wound zone 127 and/or epitheliating wound zone 128. Peri-wound zone 127 may be inflamed or otherwise irregular due to the adjacent open wound 120. The illustrated wound site 120 is further shown to have a flexible tape ruler 103 placed near to it. In one embodiment, a color photograph (e.g., a digitized color image) is taken of the combination of the wound site 120 and adjacent ruler 103 so that dimension of various parts of the wound can be determined with reference to the adjacent ruler 103. In one embodiment, the adjacent ruler 103 extends to identifiable landmarks preexisting or added (e.g., marked) on the patient's body so as to thereby create a reproducible frame of reference and the taken image of the wound 120 and ruler 103 includes the identifiable landmarks.

Conventional wound dressings attempt to cover the entirety of the open wound site 120 and slightly beyond with a homogenous dressing material such as woven cotton so as to at least prevent dirt and new bacteria (102b) from entering the open wound. By contrast and more recently, as mentioned above, it has been proposed to map and characterize a wound site such as 120 according to a variety of parameters including for example, by indicating which areas (zones) of the wound have too much liquid in them (too wet) and which have too little (are too dry) and which have a moisture concentration which is just about right. This characterization of wound zones may be performed by a health care provider (e.g., doctor) with or without assistance from objective automated measurement tools that measure for example, local water concentration, local pH, and so forth. Referring to FIG. 1B, shown is a first wound characterizing plot 150 that indicates relative degree of excess moisture (in the direction of the +W wetness axis) and relative degree of excess dryness (in the negative W direction) as plotted relative to respectively mapped X and/or Y geographic coordinates of the wound site 120. Wound center region $R_0$ is indicated to be too wet and the relative excess amount of liquid production (exudate discharge) is defined by the shape of waveform section 151. Epitheliating wound zone $R_1$ is indicated in this example to be too dry and the degree of excess dryness (not enough clean moisture) is indicated by the shape of waveform section 152 as distributed over its respected X and Y coordinate points. Waveform section 153 may be read to indicate that moisture levels for the peri-wound zone 127 and adjacent healthy skin zone 130 of respective regions $R_2$ and $R_3$ are just about right prior to administration of a dressing (conventional or otherwise) onto the open wound site 120 and slightly beyond.

One of the dressing design parameters that can be associated with a respective wound site mapping and characterizing plot (e.g., plot 150 of FIG. 1B) is the rate (R) at which liquid (moisture) should be removed from the underlying wound zone by one or more material layers of a corresponding, custom-designed wound dressing (see briefly, custom tailored dressing 209 of FIG. 2). Such liquid removal profiles may be prescribed by a health care provider and/or automatically by a preprogrammed computer. FIG. 1C shows an example of such a wound dressing function map in the form of a desired-liquid-removal rate plot 160. The positive removal rate axis (+R) indicates a relative desired liquid removal rate for the respective X and Y coordinate points of the mapped wound site 120. Waveform section 161 indicates that a relatively fast or high rate of liquid removal should be provided for the coordinates of exudating zone $R_0$ so as to counter-match the degrees of excessive wetness (+W) indicated by waveform section 151 of plot 150. Similarly waveform section 162 indicates that an inverse moisture removal function (−R), in other words at least a blocking of excess drying if not injection or donation of additional moisture (and possibly medicines) should be provided in corresponding parts of region $R_1$. The liquid removal/sourcing function plan 160 for the given wound site 120 indicates that the current rate of moisture removed by natural forces at wound zones $R_2$ and $R_3$ is about right and should not be changed as is indicated by waveform section 163.

One of the ways in which moisture rates can be controlled is by appropriate selective patterning of an out-gassing layer (see briefly 220 of FIG. 2) in a multi-layered custom dressing. Details regarding how permeation from different areas of an out-gassing layer can be selectively controlled are provided in the above-cited U.S. Ser. No. 11/972,451 ("Wound Dressing with Controllable Permeability") whose disclosure is incorporated herein by reference. Briefly, microfiber pores may be closed or clogged in selected areas by thermal melting of polymer microfibers and/or by other means so that they no longer allow permeation of out-gassing vapors therefrom.

FIG. 1D shows a third plot 170 indicating how out-gassing permeability (+P) of such an evaporation control layer (e.g., 220) can be selectively controlled to match the desired liquid removal rates versus geography as indicated by planning curve 160 (FIG. 1C). Wave section 171 indicates that water vapor should be allowed to out-gas rather rapidly so as to match the desired liquid removal rate of wave section 161. As water vapor leaves from the out-gassing layer, additional room for further absorption is made available in a lower water absorbing layer (see briefly layer 230 of FIG. 2). Thus liquid removal rate can be increased by increasing vapor permeation rates of the overlying permeation control layer. (Of course this depends on external humidity, air temperature, etc.) Waveform section 172 of FIG. 1D indicates that areas corresponding to region $R_1$ should be partially or fully blocked from allowing moisture to leave thus preventing excessive drying. Wave section 173 is provided in FIG. 1D merely for purpose of symmetry with corresponding sections of FIGS. 1B and 1C.

With regard to waveform sections 163 and 173 (desired no changes), it will soon be explained in more detail how such non-change of conditions may be guaranteed for the healthy skin or peri-wound sections adjacent to an open wound site 120. It will soon be explained in detail how such adjacent skin tissue can be protected from being damaged by exudates 141

(FIG. 1A) emerging from the wound and/or from being damaged by moisturizing liquids (e.g., medicines and/or pure normal saline water) applied to the wound as part of a treatment plan.

However, before delving into these details, attention is first focused to FIG. 2 where a schematic diagram provides an overview of a custom-tailored product 200 that may be fabricated by automated means in accordance with the present disclosure. The custom fabricated product 200 includes a custom-tailored wound dressing 209 that is fabricated in accordance with the present disclosure to include, for example, custom tailored barriers 262 that are shaped and dimensioned to protect wound adjacent healthy skin when the dressing 209 is later applied to a corresponding wound (204c). The wound dressing 209 is further custom patterned to provide different functionalities for different zones of an individual open wound site such as 120. The product 200 includes a protective packaging 206/207/208 which is provided to sealing-wise house the dressing 209 and maintain the dressing in a clean or sterile environment prior to application to a corresponding wound (e.g., 120). The protective packaging 206/207/208 also functions to route the contained dressing 209 to the correct patient and corresponding wound. In one embodiment, the clean/sterile packaging 206/207/208 has a first sheet or layer 206 which is also referred to here as the base packaging sheet even though layer 206 is shown to be topmost relative to the +Z reference frame. Packaging 206/207/208 also has a second sheet or layer 208 (optionally thinner than layer 206) which is referred to here as the topside packaging sheet even though layer 208 is shown to be bottommost relative to the illustrated +Z reference frame. Reasons for this will become clearer when the automated manufacturing process is described below (see briefly FIG. 3A). Packaging sheets 206 and 208 are flexible, gas impermeable and sealed together at their peripheries by applying appropriate pressure to a flexible, gas impermeable and pressure sensitive adhesive (PSA) ring 207 that is preformed on topside sheet 208. The PSA ring 207 is activated by the appropriate level of pressure to sealing bond the first and second packaging sheets 206 and 208 to one another at their peripheries.

The base packaging sheet 206 may include an integral base labeling layer 205 that is provided as an integral part of sheet 206 where label layer 205 may for example be a thermally printable white surface onto which a thermal printer (not shown) can automatically print identification and other information as desired at the time that sheets 206/208 are sealed together by PSA seal 207 and dispensed with custom dressing 209 enclosed between sheets 206/208. The top side package sheet 208 may be composed of a transparent flexible plastic material which is gas impermeable as well as being impermeable to microbes or other contaminates. Packaging combination 206/207/208 is shown in FIG. 2 with its base sheet 206 on top (highest in the +Z direction) and its top side sheet 208 below because that shows the orientation of the enclosed dressing 209 as the latter is applied to a corresponding wound (e.g., 120). In other words, when dressing 209 is removed from the package and applied, an uppermost, liquid-permeable mesh layer 210 of the dressing is positioned on top to serve as an interface with the outside environment (102) and a liquid-permeable wound contacting layer (could be 250 or 240 or 230) is positioned below to interface with the wound and/or adjacent skin. During manufacture however, the base packaging sheet 206 is deposited first on a fabrication stage (see briefly 306-305 of FIG. 3A) and then the liquid-permeable mesh layer 210 as well as an integrally attached out-gas control layer 220 (liquid-impermeable) are deposited on the base packaging layer 206 as shall be detailed below.

Product 200 may optionally include a computer-printed adhesive identification label 204 attached to the exterior of the topside package sheet 208. In one embodiment, topside label 204 is automatically printed and thereafter attached to sheet 208 immediately after the package is sealed and dispensed for routing to a given wound on a given individual patient. The product 200 may thus have at least two patient identifying indicia formed thereon, one by means of topside label 204 and a second by means of base label 205. Optionally, a third label (not shown) with mailing information thereon and a backside adhesive covered by a peel off wax paper may be attached to label 204 by a perforated paper coupling. When product 200 is being inserted into a mailing envelope (not shown), the user tears off the third label (not shown) along the perforations and sticks it to the outside of the mailing envelope. Optionally, further identifying indicia may be burned into an underneath side of layer 220 (or top of sheet 315 as the latter is shown in FIG. 3A). Although not shown in FIG. 2, layers 210 and 220 generally extend out in the X and Y lateral directions substantially further than layer 230 so that layers 210 and 220 can be adhesively or otherwise secured to healthy skin. The underside of this extended part of layers 210/220 may have patient identifying and wound identifying indicia burnt thereon with a polymer burning tool or otherwise formed thereon.

An example of patient/wound identifying and other functional indicia that may be provided is shown by way of example for the top side label 204 in the form of a magnifying glass symbol enlarged view 204. As seen, label 204 may include a first identification 204a of the specific patient for which the enclosed and custom tailored dressing 209 has been fabricated and is intended to be routed to. The label may further provide routing information 204b indicating to whom next and how the sealed product 200 is to be routed. For example it may indicate that the product 200 is to be shipped directly to the patient's home or that it is to be routed indirectly to the patient by first hand delivering it to a pre-assigned caregiver (e.g., licensed nurse practitioner) who will then carry it to and apply it to the patient. The indicated method of routing may be by way of regular parcel post mail or by special delivery rush courier or by other means. The top side label 204 may further identify the specific wound (e.g. 120) for which this specific dressing has been designed. Wound location identification may include one or more graphic images 204c such as schematic diagrams of a human body front and back with a spot marker indicating exactly where the wound dressing 209 is to be placed on the of the given patient 204a and in what orientation. Wound location identification may further be provided by color coding of the topside label. For example, a patient or care giver may be taught that a green-colored label means this dressing goes on the back while a yellow label means the enclosed dressing goes on the left leg. Label 204 may further provide dates 204d on which the custom dressing 209 is to be applied to the wound and thereafter respectively removed. In some instances, a plurality of sealed products like 200 are custom formed at a same time under coordination of a care coordinating computer program (see briefly 507b of FIG. 5B), then individuality sealed and sent in unison to the patient or nurse for sequential application over a doctor prescribed sequence of dates. In such a case, each dressing may have its own one of sequential and unique identification numbers (e.g., Rx numbers, not shown) included on label 204. Information 204d indicates the doctor-prescribed application and removal dates for its contained dressing.

The attached label 204 may further include more detailed instructions 204e for application and/or removal of the correspondingly enclosed dressing 209. For example, the prescribed application of the custom tailored dressing may call for provision of medicines or ointments to the wound or dressing prior to applying the dressing to the wound or the prescription may call for addition of such medicines, ointments, oils, etc. to the dressing 209 after it is applied to the wound. In one embodiment, an address of an internet web page (e.g., www.private123.com) is given on the label and when opened, the identified web page (e.g., a password secured page) provides detailed instructions for application and removal as well as a repeat of the patient identification information 204a and wound identification information 204c provided by label 204. Thus the whole of product 200 is seen to be a functional combination that is operative for routing a custom fabricated wound dressing 209 in sterile or clean form to the intended patient (101) and intended wound (120) for application thereto in a prescribed orientation at the doctor prescribed date and time 204d and with optional addition of doctor prescribed addends (as specified by instructions 204e). In one embodiment, the custom wound dressing 209 and enclosing packaging 206/207/208 as well as associated routing and/or use information (204a-c, 204e) are automatically produced under control of a single coordinating computer program (e.g., 307b executing for example in a single coordinating computer—see 307 of FIG. 3A) so as to assure that the correct dressing will be routed to the correct patient and applied to the correct wound at the right time with correct associated usage instructions. This helps to reduce the possibilities for foul up in each of the various steps that span from treatment formulation to treatment delivery. A user-friendly combination 200 is thus automatically manufactured and provided with associated informational indicia integrated thereon for routing the enclosed dressing 209 to the intended patient 204a and to the intended wound 204c and for application of the dressing on the wound as intended by the prescribing care provider (e.g., doctor).

Referring to the topmost dressing layer 210 in FIG. 2, and to the magnification 201 thereof, this topmost layer 210 may be fabricated as a nonwoven mesh of polymer microfibers where the microfibers are hydrophobic in nature, nonsoluble in water and provide a strong outer and scuff-resistant interface for interfacing with the external environment (102 of FIG. 1A). Average pore size between the intersecting microfibers of interface layer 210 is sufficiently large to easily let bulk water droplets through and as well as gases (e.g., water vapor) through. Any of a variety of relatively strong polymers may be used for forming microfibers layer 210, preferably those with low friction and good scuff resistant properties. Methods for forming microfiber meshes are disclosed for example in the above-cited U.S. Pat. No. 7,105,058 whose disclosure is incorporated herein by reference. The present disclosure is not limited to the methods described in U.S. Pat. No. 7,105,058.

The second layer 220 of dressing 209 is also composed of a non-woven mesh of hydrophobic intersecting polymer microfibers. However the average pore size between the microfibers of layer 220 (see magnification 202) is extremely small; generally less than about 0.5 micron and better yet, less than about 0.2 micron. As such, the pores are sufficiently small to block microbes and bulk water droplets from passing through. However these micro pores are sufficiently large to let one or more desired gases through such as water vapor. Thus, the second layer 220 forms a liquid impermeable and microbe impermeable barrier layer that can block infected exudates (e.g., 141 of FIG. 1A) from rising out of the wound 120 in the +Z direction and thereafter continuing to ooze out through the topside of the dressing 209. The second layer 220 also prevents contaminated liquids or particles (e.g., 102b of FIG. 1A) from entering into the dressing in the −Z direction. Different regions of layer 220, such as 222 may be custom patterned (e.g., selectively clogged) to further limit or to totally block out-gas permeation through those custom adjusted zones (222). Examples of how such custom control may be realized are disclosed in the above-cited U.S. Ser. No. 11/972,452 ("Wound Dressing with Controllable Permeability") whose disclosure is incorporated herein by reference. The disclosed methods include selective heat melting of a bottom portion (as shown by area 222 in FIG. 2) of layer 220 with hot sterile air or with laser beams or other such selective heating means so as to melt the fibers in those selected zones and thus create a non-permeable film areas thereat. In one embodiment, second layer 220 is provided as an integrally fused part of a multilayer sheet material that also includes top layer 210. The fused multilayer sheet material 210/220 is stretched over a fabrication stage (see briefly 305 of FIG. 3A) and a custom shaped portion thereof is cut out with a cutting tool (301) and dropped onto the stage under directions of a fabrication coordinating computer 307. In one embodiment, the first and/or second layers 221/220 have one or more through holes such as 225 formed therethrough (or perforations whereby cylindrical section 225 can be torn out) so as to allow coupling of liquids through the through holes 225 to or from an external liquid storage means. The through holes or tear-out perforated sections 225 may be pre-sealed with an impermeable polymer film that can be selectively removed with a corresponding solvent during automated dressing fabrication. This is done under direction of a fabrication coordinating computer 307 when the through hole or port section 225 is intended to be opened up for operative coupling to an external liquid storage means (e.g., a foam pad that is pre-soaked with sterile normal saline solution).

Still referring to FIG. 2, a third layer 230 of the custom dressing 209 is composed of hydrophilic and thermally meltable microfibers. Magnification 203 shows that the pores between the intersecting polymer microfibers of layer 230 are of medium size so as to let through both bulk liquid droplets and gases. The general use of this third layer 230 is to either absorb liquids into itself (into its pores) and/or to store and donate clean moisturizing liquids into to the wound depending on wound region and its treatment needs. The to-be-absorbed liquids may include exudates 141 emerging from the underlying wound As shall be detailed shortly, flow control barriers 260 such as those for controlling flow of aqueous solutions may be selectively formed as custom patterns that extend either entirely through the thickness of this third layer 230 or extend partially through the thickness of layer 230 as desired and in desired locations thereof. In one embodiment, barriers 260 subdivide third layer 230 into a central zone (corresponding to $R_0$ of FIG. 1A) that is kept dry during fabrication and a peripheral (but not to the edge) zone that is filled with sterile saline solution during fabrication. Upon application of the custom dressing 209 to a corresponding pre-mapped and pre-characterized wound such as 120 (FIG. 1A), the pre-moisturized peripheral zone aligns with and donates moisture to a first wound zone that had been pre-characterized as a too dry wound periphery (e.g., 125). The non-moisturized dressing center aligns with and absorbs exudates from a second wound zone that had been pre-characterized as being an excessively wet. Thus each wound zone is specially treated according to its needs.

In some embodiments, the packaged custom dressing 209 is composed of just the first three illustrated layers 210, 220, and 230. In other embodiments additional layers may be included such as the illustrated fourth layer 240. Layer 240 is composed of hydrophilic microfibers with capillary soak up capabilities for drawing liquids up or down through layer 240. Layer 240 has a corresponding bottom major surface 241 and layer 230 has a corresponding bottom major surface 231. When a given liquid is transported into or out of the bottom of layer 240, the bottom area for flow of that liquid through bottom surface 241 is not necessarily the same as the surface area used for moving that same liquid (e.g., exudates) through the bottom 231 of layer 230. Funneling or other liquid flow controlling barriers such as 260 may be fashioned so as to define different surface areas for liquid inflow or outflow at respective bottom surfaces 241 and 231 of respective layers 240 and 230. Additionally or alternatively, partial flow barriers such as 262 may block parts of lower surface 241 from passing liquids therethrough as will be detailed below. In either case, by adjusting the amount of surface area 241 available for transport of different liquids through the bottom of layer 240 and by adjusting the pass through surface areas at interface 231, the designer of a custom dressing 209 may alter the rates at which different liquids move from one layer to the next and/or may alter the amounts of liquids absorbed or donated from one layer to the next. Thus the ability to create custom barriers like 260 and 262 in the composite wound dressing 209 gives the dressing designer an ability to better custom tailor the functions provided by the dressing 209 to match the treatment needs of a corresponding individual wound 120.

The fifth, wound-interfacing layer 250 is also optional. It is shown for the purpose of demonstrating that different areas of the dressing that interface with the actual wound may have different local interface chemistries 252 depending on which chemicals are custom tailor wise donated into region 252 or removed from region 252 and also depending on the differing rates at which these various chemicals are transported out of or into the respective dressing regions.

The actual wound itself which alignably underlies interface surface 251 is of course not present inside packaging 206/207/208 but it is nonetheless shown in phantom in FIG. 2 in order to show how a first pre-characterized wound zone 291 that is deemed to be too wet and thus requiring absorption of exudates therefrom aligns with a funnel enlarged absorbing volume in layer 230 and with a high gas permeation area of layer 220. It also shows how a second pre-characterized wound zone 292 that is deemed to be too dry and thus requiring of the dressing to donate moisture to that area 292 is aligned with a barrier bounded, liquid donating volume of layer 230 (bounded by custom formed barrier 262) and overlaid by a blocked gas permeation area 222 of permeation control layer 220.

With the overview of product 200 now in place, attention is directed to a specific automated manufacturing process. FIG. 3A is a perspective view showing a custom tailored dressing 309 at an intermediate state during its automated manufacture. The automated manufacturing process 300 includes the provision of a supporting stage 305 such a rigid flat metal plate. A base sheet 306 of a to-be-formed sealing package is stretched out over the stage, flattened thereon by for example moving a combination of supply and take up reels towards the supporting stage 305 or vise versa. Each step in the automated manufacturing process 300 may be controlled by a fabrication and packaging coordination program executing for example on a local coordination computer 307. Computer 307 is understood to have appropriate hardware and software components including one or more data processors, memory and I/O interface circuitry (represented by 307a) for interfacing with and controlling the various computer controlled mechanisms described herein including a motorized means (not shown) for dispensing base packaging sheet 306 on the support stage 305.

In a next step of the automated process 300, a multi-layered hydrophobic polymer microfibers sheet (not shown) is dispensed in stretched form above and vertically spaced apart from the base package sheet 306. Such dispensing of the multi-layered hydrophobic polymer microfibers sheet is performed by a corresponding sheet dispenser (not shown) under control of computer 307. A pre-specified shape 315 (e.g., rectangle with rounded corners) of prespecified dimensions is cut out from the dispensed and overlying hydrophobic multi-layered sheet (not shown) under control of computer 307, and then deposited (e.g., dropped) on a prespecified region of the base package sheet 306 and flattened thereto. Multi-layer sheet section 315 corresponds to layers 210 and 220 of FIG. 2. In one embodiment, a high temperature polymer cutting tool (vaporizing tool) 301 is used to cut out the shaped pattern 315 from a larger dispensed sheet. The polymer cutting tool 301 includes a ceramic cylinder that supports a twisted nichrome wire emerging from a bottom portion thereof. The nichrome wire (e.g. having FIG. 8 twisting) and its holding ceramic tube are operatively coupled to and translated by an X-Y position translator 302 that is controlled by coordinating computer 307. The cutting tool 301 is further connected to and translated by a computer-driven Z translator 303. Moreover, a computer-driven electric switch 304 selectively couples electrical power to the nichrome wire so as to turn its heating on and off, where the on state produces a polymer vaporizing temperature that vaporizes the material of sheet section 315. In operation, the cutting tool 301 is first positioned by the X-Y translator 302 above a start point of a computer-defined cutting path. The heat is turned on (by actuating switch 304) and then the Z translator 303 lowers the tool 301 to begin a polymer vaporizing traverse along a predefined X-Y cutting path. When the predefined cutting path is finished, the Z translator lifts the tool 301 up and the heating switch 304 is turned off. The shape and dimension of the hydrophobic multilayer sheet section 315 is thus defined to correspond to a pre-mapped and pre-characterized wound or wound zone. During the cutting, positive air pressure is maintained in the process chamber (not shown) that houses stage 305 and tool 301 so that the vaporized polymer material created by tool 301 escapes to a lower pressured ambient atmosphere.

In a next computer controlled step, out-gassing permeation rates through different areas of the cut out section 315 are optionally varied in accordance with the above-cited U.S. Ser. No. 11/972,451 whose disclosure is incorporated herein by reference. In one embodiment, a computer controlled hot air blower (see 408 of FIG. 4A) is used to selectively melt polymer fibers in select subsections of cut out sheet section 315.

Next, a second fibrous sheet composed of hydrophilic microfibers is stretched over the precut hydrophobic sheet 315 by action of a corresponding sheet dispenser and this second fibrous sheet is pattern cut under control of the coordinating computer 307 and with use of tool 301. The cut out section 330 of the second dispensed fibrous sheet (not shown) is thereafter dropped onto to the stacked combination of base package sheet 306 and the cut out hydrophobic multilayered sheet 315. Cut out section 330 is fastened to earlier cutout 315 by spot heat welding or otherwise. In one embodiment, the automatically shaped, dimensioned and deposited hydrophilic microfibers sheet 330 corresponds to layer 230 of FIG. 2.

As part of the design for the custom tailored cutting of the hydrophilic microfibers sheet 330, a certain overlay region (OL) is pre-specified where the custom-shaped sheet 330 will overlay on healthy or peri-wound skin. The shape and dimensions of the pre-specified overlay region (OL) may be stored in an operational memory of computer 307.

FIG. 3B is a side sectional view showing how the wound-matching hydrophilic microfiber layer 330 of FIG. 3A is intended to align with overlay peri-would zone 327 when the dressing 309 is later aligned over and applied to its corresponding wound 380. Additional details in FIG. 3B are that the hydrophobic multilayer sheet 315 may include a wide-pores layer 310, an ultra narrow-pores layer 320 and a spot weld-forming lowest layer 321. The melting temperature of fibers in lowest layer 321 is lower than the melting temperature of fibers at the bottom of layer 320 or the top of layer 330. Thus, when a computer-controlled spot welding tool (not shown) having a temperature lower than the melt temperatures of layers 330 and 320 but higher than the melt temperature of layer 321 is compressively applied at a pre-selected weld point 323, fibers in layer 321 melt and infiltrate into layer 320 above and layer 330 below to thus form a spot weld of molten material extending between and into layers 320 and 330. When the welding tool is removed, the weld 323 solidifies and thus securely attaches sheet 330 to layer 320. Prior to formation of the weld 323 however, different areas 372 of layer 321 other than where the spot weld 323 will be formed may optionally be premelted into layer 320 so as to clog gas permeating pores in layer 320 and thus custom adjust gas permeation rates through layer 320. These selectively premelted areas are represented by ellipses 372 and 372'.

A problem can emerge when a multilayer dressing such as that shown in FIG. 3B is applied to a heavily exudating wound 380. The liquids 381 which rise up out of the wound 380 and into the lowest layer 330 (e.g., hydrophilic layer) of the dressing may include undesirable components such as pus, bacteria, and toxic chemicals generated within the wound and removed therefrom as part of absorbed upflow 381. Because layer 330 in its unpatterned form is isotropically hydrophilic, the absorbed exudates 381 can continue to diffuse laterally along phantom path 382 and thus migrate to the overlay area (OL) where dressing material 330 directly overlays on the peri-wound zone 327 and/or on adjacent healthy skin. These laterally migrating exudates 382 may damage or degrade the overlaid peri-wound zone 327 or adjacent healthy skin area (not shown) and thus undesirably cause an expansion of the wound as opposed to promoting healing.

Referring to FIG. 4A shown is a perspective view of a next step 400 in the automated process 300-400 for fabricating the custom-patterned dressing under control of coordinating computer program 307b. The further refined dressing is now denoted as 409. In accordance with one aspect of the present disclosure, a liquid blocking barrier 445 is custom formed within the overlay region (OL) of the hydrophilic microfibers sheet 430 to block laterally diffusing and potentially harmful liquids such as exudates 482 (or moisturizing saline solution loaded into dressing region R1) from reaching and possibly degrading the overlaid skin or peri-wound areas (OL). This liquid blocking barrier material 445 is preferably formed from a material 401a which is itself non-toxic and not damaging to the overlaid skin zone 327 that is will lie over. Examples of flow blocking materials that may be used include water repelling materials (hydrophobic materials) such as silicones, silicone oils, mineral oils and vegetable oils. One or more of these skin-safe but water blocking materials may purchased or custom formulated (e.g., by appropriate distillation) to provide desirable viscosity, surface tension, capillary attraction and/or other properties as shall be explained shortly.

The chosen or custom formulated water repellant substance or substances is/are picked to have sufficiently moderate viscosities so that they can infiltrate relatively quickly into the microfiberous matrix of the liquid transport or liquid storage layer 430 in which it/they are to be embedded. The combined characteristics of layer 430 and the utilized water repellant substance(s) 401a are such that after liquid 401a infiltrates in the +Z direction into a desired area of the target layer 430 (e.g., the wound-interfacing layer 430) to a desired depth, liquid 401a becomes resistant to further migration and it substantially maintains its post-infiltration shape and location under normal (e.g., room) temperature and/or other normal operating conditions. In other words, after having been deposited in the +Z direction onto the upward facing surface 431 of cutout sheet 430 of the FIG. 4A during the automated manufacturing process 400, the infiltrating blocking material 445 holds itself together within the infiltrated porous layer 430 under normal dressing-use conditions due to one or more of viscosity effects, surface tension effects, capillary drawing effects and/or other effects so as to substantially maintain an outline of its deposited pattern and to thus function as a barrier against the flow of aqueous fluids (e.g., exudates) therethrough. In one embodiment, a silicone with a viscosity in the range of 1 centiStoke to 1000 cSt is used with a nominal value of around 5000 cSt. In another embodiment the viscosity of the utilized silicone is in the range of 100-1000 cSt with a nominal value of about 500 cSt. The specific viscosity used will vary from case to case depending on the porosity and/or other characteristics of the wound interfacing layer 430. In one embodiment, medications or vitamins (e.g., vitamin E) are mixed in with the utilized silicone or other water repelling liquid 401a so as to promote skin health at the region where the skin overlying outer barrier 445 is formed to contact with a corresponding skin area.

Intrinsic silicones tend to be colorless. However, non-toxic colored dyes may be added to them. See for example U.S. Pat. No. 4,737,537 (Colored Silicone Composition) whose disclosure is incorporated herein by reference. See also WO/2005/102675 (Curable Colored Inks for Making Colored Silicone Hydrogel Lenses—U.S. provisional 60/564,024) whose teachings are further incorporated herein by reference. In accordance with one aspect of the present disclosure, silicones or other water repellant barrier liquids may be optionally colored by adding non-toxic dyes thereto so as to form readily visible boundary lines or curves (e.g., 445 and 443 of FIG. 4A) on the wound facing surface 431 of a custom wound dressing. Users may then be instructed to infuse water, saline solution or specific medications into visibly bounded regions (e.g., R0, R1 of FIG. 4A) on a custom tailored dressing. Colored silicones need not be used exclusively for forming barriers. It is within the contemplation of the present disclosure to mark the face of a wound contacting dressing layer with pre-colored silicones or the like, whether while simultaneously creating a barrier line with the colored liquid material or not.

Deposition of the fluid flow barrier material 401a and its infiltration into the wound-interfacing layer 430 to form the embedded barrier 445 may take on many forms. As already mentioned, in one embodiment, the viscosity of the water repelling material 401a is chosen so that it can infiltrate into the pores of the microfibrous material 430 fairly rapidly at room temperature and yet will remain in its infiltrated original shape within the microfibrous polymer material 430 after infiltrating due to surface tension effects, capillary effects and so forth.

In a second embodiment, a viscosity-lowering solvent is mixed together with an otherwise high viscosity, water repelling material. The mixture 401a of solvent(s) and water repelling material(s) is then selectively deposited as drops over the overlay region (OL), for example by using a repellent dripping tool 401 whose position and drip rate are controlled by coordinating computer 307'. As seen in FIG. 4A, dripping tool 401 of one embodiment is operatively coupled to and translated by the same computer-driven X-Y translator 402/302 as used for controllably translating cutting tool 301 of FIG. 3A. The repellent dripping tool 401 is also operatively coupled to a computer-controlled drip rate controller 403. Droplets 401a are released at an appropriate rate corresponding to movement by the X-Y translator 402 after the translator has brought the dripping tool (capillary) over a desired start point where the to-be-embedded barrier 445 is to be formed. After the water repellent material 401a with its included viscosity-lowering solvent infiltrate into the wound-interfacing layer 430 at normal room temperature, the material is heated to an above-normal temperature but not one at or above the melt temperature of the dressing polymers. The raised temperature volatilizes and removes the viscosity-lowering solvent and/or at the same time temporarily reduces the viscosity of the left behind barrier material so that the latter may diffuse vertically and/or laterally by a predetermined amount. Localized heating may be provided for example with an X-Y driven hot air guiding tube 408 such as shown in FIG. 4A. After the solvent is driven off and temperature of the left behind water-repelling material 445 returns to room temperature, the viscosity of this left behind water-repelling material 445 is substantially reduced and its self coherence is increased due to removal of the solvent and removal of localized heating. As a consequence, material 445 retains its post-deposition and post-infiltration shape and thickness as well as its relative position within the dressing material. By overlapping deposited drops 401a, a continuous barrier 445 may be formed that fully covers the to-be-protected surrounding skin of a given wound. Of course, the protective barrier may alternatively be patterned to be other than fully continuous and fully covering (e.g., it may be patterned as a plurality of spaced apart dots). The specific pattern created under control of fabrication coordinating computer 307 may vary and depend on the specific treatment plans devised for the corresponding wound dressing 409 by a prescribing health care provider.

In yet another embodiment, water repellent material 401a of relatively high viscosity is dripped on top of surface 431 at desired positions where the high viscosity is such relative to the pores sizes of layer 430 that the dripped on material 401a does not readily infiltrate into the microfiberous matrix of layer 430 but instead remains puddled on its top surface 431 at the point of deposition (e.g., in the OL region). Then the viscosity of deposited material is temporarily lowered by heating with a heating tool such as 408 (e.g., to a temperature above 25° C. but below the melt temperature of layer 430). The heated barrier material 401a then temporarily decreases in viscosity due to the raised temperature and infiltrates into the microfiber matrix of layer 430 to become imbedded therein. When the heat is removed, the viscosity of the infiltrated material 445 increases again and it thus becomes relatively fixed in its embedded position within layer 430. In one embodiment, heating tool 408 receives filtered air through a flexible plastic tube 450. The air heating tube and an included resister (heating element) thereof are translated by X-Y translator 402/403. Electric heating of the resistive element in tube 408 is controlled by a computer-driven on/off switch 404. Filter 461 protrudes through a relatively air-tight chamber casing 460 where the later houses the in-fabrication dressing 409. The air filter 461 has pore sizes sufficiently small to block out microbes from entering into the sterile interior environment of the casing 460. Blower 470 maintains positive air pressure within the casing interior so that unclean air cannot enter. Prior to use, the barrier forming material 401a is kept in essentially sterile condition so that its introduction into layer 430 will not inadvertently contaminate the dressing with harmful microbes. In one embodiment, prior to use in fabricating dressings, one or more of the barrier forming material 401a, the drip tool 401 and the heating tool 408 (as well as flexible tube 450 and filter 461) are subject to gamma irradiation of sufficient intensity to render them medically sterile.

In addition to forming the outer protective barrier 445 for blocking harmful fluids from reaching the skin overlay region OL, additional custom shaped and dimensioned water repellent barriers such as 443 may be formed through the thickness of the wound-interfacing layer 430' as shown in FIG. 4B. In the illustrated example, dressing region R1 corresponds to epitheliating wound zone 128 of FIG. 1A. Since in the given example it is desirable to keep the epitheliating wound zone 128 somewhat moisturized while preventing the exudating discharge 381 from the center of the wound 140 from reaching epitheliating wound zone 128; the inner barrier 443 is custom patterned to fully surround exudating wound zone R0. Additionally, after the inner barrier 443 is embedded into layer 430', a moisture providing liquid such as clean water or saline solution or a medicine containing solution is deposited into the barrier embraced, intermediate region R1 of layer 430'. Outer barrier 445 keeps this deposited moisturizer from reaching the overlaid skin of overlay zone OL. Inner barrier 443 keeps the deposited moisturizer from being contaminated by exudates that enters central region R0 of layer 430'. The gas impermeable patterned region 472 overlying and engaging with barriers 443 and 445 keeps the deposited moisturizer of dressing region R0 from evaporating away into the ambient. Accordingly, the prescribed moisturizer in dressing region R0 is directed to only the pre-mapped wound zone where it is intended to be applied and it is blocked from dissipating wastefully or harmfully into other areas. It is to be noted here that even in the case where the prescribed moisturizer in dressing region R0 is simply clean water, the latter can damage or degrade adjacent skin if the skin is exposed to the water for too long of a time. However, the silicone or other nontoxic material used for forming the outer barrier 445 protects the overlaid skin and blocks it from being damaged from harmful liquids including moisturizing water and/or exudating discharge 482. It is also to be noted that during fabrication, the inner barrier-surrounded dressing region R0 is kept dry due to presence of inner barrier 443 while one or more moisturizing liquids are selectively deposited into adjacent dressing region R1. The kept-dry, inner dressing region R0 may then absorb a maximum amount of exudates when it is later applied to the corresponding wound 480. Water vapor 483 may readily evaporate out from the absorbed exudates 482 and escape into the ambient through permeation control layer 320 so as to make room for absorption of additional exudates into dressing region R0. In one embodiment, after the moisturizing clean liquid(s) is/are deposited into dressing region R1 with a computer-controlled selective dripper similar to tool 401, surface 431 of the patterned dressing layer 431 is covered with a peel-off wax paper or impermeable plastic sheet that traps the clean liquid(s) in dressing region R1 until the custom dressing 409 is about to be applied to its corresponding wound 480. If such a peel-off sheet is included in the packaged product (see FIG. 2), the corresponding dressing usage instructions will typically include an instruction to remove the peel-off sheet prior to application to the corresponding wound 480.

Figure 5A:
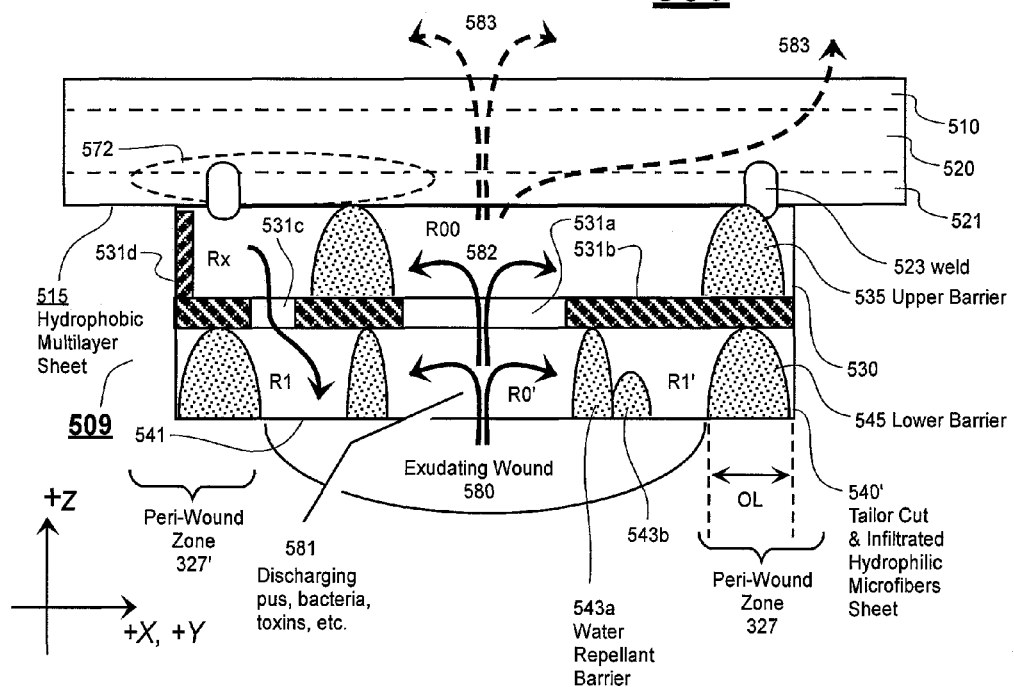
FIG. 5A is a side sectional view showing how fluid blocking barriers may be formed in multiple layers of hydrophilic absorbent sheets so as to direct flow of different fluids to or from pre-identified and pre-characterized wound zones.
Figure 5B:
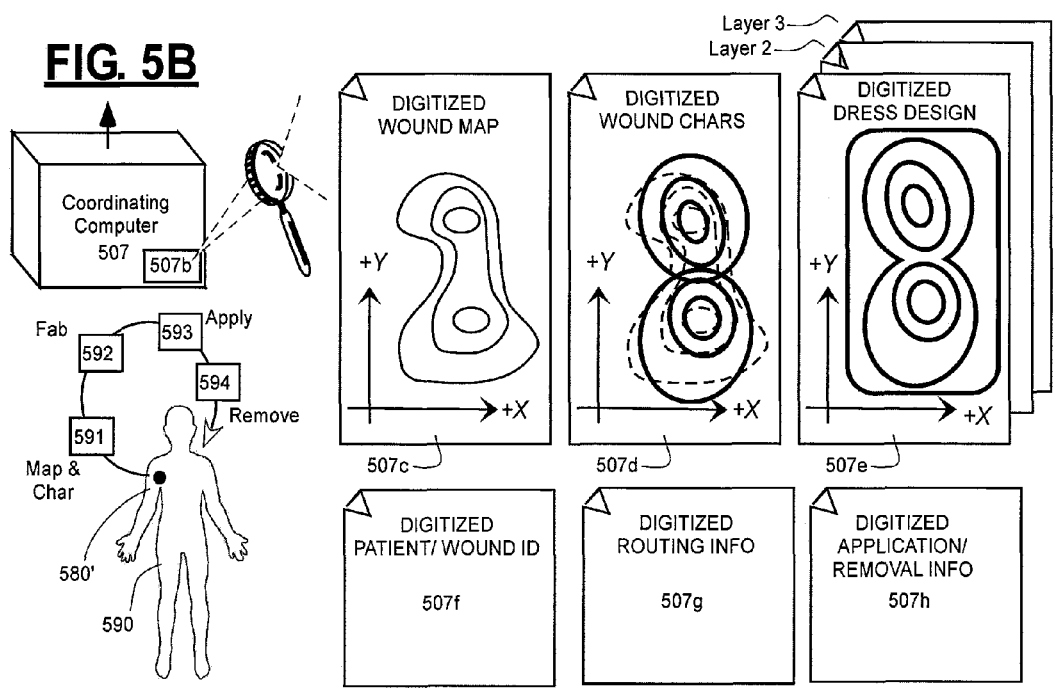
FIG. 5B is a schematic for showing how a coordinating computer program can assure a complete circle of customized dressing creation and usage, from wound mapping and characterization, to custom fabrication of a matching dressing and subsequent routing of the fabricated dressing for application to the correct wound on the correct patient.

FIG. 5A is a side sectional view showing how more complex fluid routing and/or blocking barriers may be formed within multiple layers (e.g., 530, 540) of hydrophilic absorbent sheets in a wound dressing product 500 so as to direct flows of different fluids to or from pre-identified and pre-characterized wound zones. Here, a second hydrophilic fibrous layer 540 is cut, deposited, fastened on (e.g., spot welded on) and patterned after a previous hydrophilic layer 530 has been cut, deposited, fastened on (e.g., spot welded on) and patterned in accordance with computerized first hydrophilic layer defining data (see briefly 507e of FIG. 5B). The bulk material of the second hydrophilic fibrous layer 540 may be the same as or different from the bulk material of the first hydrophilic fibrous layer 530. In the automated patterning of the first layer 530, an upper and close bounded water repellent barrier 535 is deposited and somewhat fixedly embedded into the thickness of porous layer 530 as shown. Region R00 is designated by a corresponding computer-readable data structure (507e) as having the function of absorbing exudate 582 that enters into layer 530 while region Rx is designated by the corresponding computer-readable data structure (507e) for donating late stage moisture and/or a prescribed medicine. After the water repellent material of upper barrier 535 has been embedded into layer 530, a patterned fluid impermeable film 531b, 531d is formed on the –Z facing major surface of layer 530 and optionally (as in the case of 531d) around its peripheral edge by for example depositing a hardenable polymer film material or by melting selected parts of the –Z facing major surface (531) of layer 530 at desired positions. This selective patterning of the –Z facing major surface of layer 530 leaves liquid and/or gas permeable passageways 531a and 531c on that surface and between the first and second layers 530, 540 while locking the upper water repellent barrier 535 in place. Optionally, open liquid passageway 531c is then used for infusing clean water or saline solution and/or a liquid medicine into region Rx of the first hydrophilic layer 530 before next layer 540 is attached. Although in one embodiment, the laterally extending barriers 531b, 531d to liquid and/or gas flow are formed by deposition of an impermeable film laterally on the –Z face of layer 530, such laterally extending barriers could additionally or alternatively be custom shaped, dimensioned and formed by selective deposition and embedding of a water repellant viscous liquid that only partially penetrates into the thickness of layer 530 similar to the way that selectively deposited liquid region 543b (described below) only partially embeds into the thickness of next-described layer 540.

After patterning of layer 530 is substantially complete, the second hydrophilic layer 540 is then shaped and dimension (e.g., by custom cutting with tool 301 for example) and attached (e.g. spot welded to layer 530—welds not shown). Thereafter lower water repellent barriers 545 and 543a are selectively embedded fully through the thickness of layer 540 as shown. Optionally, a less viscous and thus more readily spreadable silicone or other water repellent liquid 543b is deposited into region R1' of layer 540 just before water or another moisturizer is selectively infused into region R1'. The viscosity of this more readily spreadable but water repellent liquid 543b is such that were it not for the water (or other moisturizer) consuming the remaining volume of region R1', the readily spreadable repellent liquid 543b would over short time (e.g., 15-30 minutes) begin to spread out over region R1' rather than retaining its shape as well as do barriers 535 and 543a. However, the water (or other moisturizer) that is quickly infused into region R1' after readily spreadable repellent liquid 543b has been infused, pushes the readily spreadable repellent liquid 543b up against less spreadable barrier 543a and prevents 543b from spreading out laterally as long as there is sufficient aqueous liquid present in dressing region R1' to push against readily spreadable repellent liquid 543b. On the other hand, during end stage use of custom dressing 509 on corresponding wound 580, the aqueous liquid in dressing region R1' substantially runs out and then spreadable repellent liquid 543b spreads out across the wound interfacing surface 531 of dressing region R1' to thereby close off region R1' and block moisture from being absorbed from the wound into the substantially dried out region R1'. In this way, the custom dressing 509 dynamically adapts itself to changed conditions and keeps an epitheliating wound zone (not shown) under region R1' from drying out.

While frusto elliptical section 543b has been described for one embodiment as being composed of a readily spreadable embedded hydrophobic liquid, in an alternate embodiment it constitutes a more fixedly embedded hydrophobic liquid that provides one or more functions including that of reducing the water-permeable surface area by way of which region R1' interfaces with the underlying wound 580 or defining a water-permeable passageway of desired thickness between the top of frusto elliptical section 543b and a spaced apart horizontal barrier such as the illustrated 531b. In both instances, the rounded top of frusto elliptical section 543b does not need to abut with water-impermeable horizontal barrier 531b or with the bottom of a water-impermeable layer such as 520. In other words, when it is formed, the frusto elliptical section 543b does not have to infiltrate all the way through the thickness of its supporting dressing layer 540. Depth of penetration by the precursor material (e.g., 401a) of frusto elliptical section 543b into layer 540 can be varied by adjustment of the heating temperature used to cause the precursor material (e.g., 401a) to infiltrate vertically into layer 540 or by the adjustment of heating time (for material 401a or for a volatile solvent mixed with it) or by the volume of precursor material (e.g., 401a) deposited as a drop on surface 541. When frusto elliptical section 543b serves as a baffle for reducing water-permeable space between its +Z top and an overhanging horizontal barrier (e.g., 531b), it may be used to controllably limit the flow rate of an aqueous liquid from one compartment in the dressing to another by controlling the distance between its +Z top and the overhanging horizontal barrier (e.g., 531b).

It is to be understood from the above that the present disclosure is not limited to just depositing water repellent liquids to form static barriers. Viscosity may be adjusted, for example by selectively depositing different silicones of different viscosities and optionally mixed with nonvolatile solvents so as to provide relatively static barriers in some locations of a given dressing layer and so as to provide relatively dynamic, more easily spreadable barriers in selected other locations of a given dressing layer. While only frusto elliptical section 543b has been described in one version thereof as being readily diffusible through region R1' of layer 540, a same tactic could have been used in other dressing regions Rx and R1 of FIG. 5A by infusing readily spreadable repellent liquids like 543b in respective regions Rx and R1 just before those regions are respectively filled with respective aqueous liquids (e.g., a medicine in region Rx and saline solution in region R1). Then as the respective aqueous liquids run out from their storage compartments in the dressing, the dynamically spreadable barriers (not shown) of regions Rx and R1 would spread out to close off those regions during late stage usage of the dressing 509 and would prevent undesired drying of the underlying wound zone. Note that melt zone 572 in layers 520-521 caps the Rx region of layer 530 and thus keeps the Rx region of layer 530 from drying out due to undesirable outgassing through layer 520.

Additionally, since upper region R00 of layer 530 has been kept dry by operation of upper barrier 535 and since upper region R00 is not capped by an out-gas blocking film above it, the upper region R00 of layer 530 is available to absorb large amounts of exudates from region R0' of lower liquid 540 and to readily dissipate water vapor 583 via the enlarged upper surface area of upper region R00. In other words, the surface area of the upper part (in the +Z direction) of dressing region R00 is not constrained by dimensions of underlying wound zones as much as the wound interfacing layer 540 may be. With use of vertical barriers like 543a and horizontal barriers like 531b, funneling structures may be devised for expanding the water vapor dissipating surface area made available for a given one or more wound zones. Accordingly, when custom dressing 509 is applied to wound 580, exudate flow 581 is absorbed not only into region R0' of lower layer 540 but rather it continues to migrate upwardly, passing through the intentionally left open liquid passageway 531a and then spreading out laterally into wider region R00 of upper layer 530. Note that the wider lateral area of region R00 means that it has greater volume (assuming layer 540 is not thicker than layer 530) and thus can absorb aqueous liquids at a faster rate and evaporate off water vapor 583 at a faster rate form its larger upper surface area. The availability of patternable vertical barriers like 535, 545, 543a, etc. and patternable horizontal barriers like 531b and 572 give designers of automatically fabricated custom wound dressings an enlarged number of options by way of which they can control directions, rates and timings of liquid flows going into a given wound (e.g., medicine Rx) and liquid flows moving out of the given wound (e.g., exudates 581). Additionally, by providing more readily spreadable barriers such as 543b within one or more dressing layers, designers can define dynamically closeable passageways which close up after a corresponding liquid content has run dry. Thus a wound dressing can be designed to dynamically adapt to changing conditions.

Referring to schematic diagram 5B, it is to be appreciated that a single coordinating computer program 507b can be executed either in a corresponding single coordinating computer 507 or across a plurality of networked processors (not shown) so as to assure that a matching custom dressing (e.g., 509 of FIG. 5A) is correctly fabricated for a given individual and pre-mapped wound (e.g., 580, 580') and that the same matching custom dressing is automatically packaged in a sealed package, that the dressing containing package is automatically labeled so as to be appropriately routed (593) after fabrication (592) to the same individual wound (e.g., 580') for application to the wound at a physician prescribed time point. In other words, a full circle of control and coordination may be provided from the time of wound mapping and characterization (591) to the time of dressing application (593) and the time of dressing removal (594). To do so, the coordinating computer program 507b may logically interlink a plurality of data files or other data structures including but not limited to: a digitized wound map or image 507c of the specific wound (which map corresponds to a predefined physical reference frame such as one formed by specific X and Y coordinates on the patient's body); digitized wound characterizing maps and/or plots 507d (see also FIGS. 1B-1D); digitized, layer by layer, dressing design maps 507e; digitized patient identifying and wound identifying data 507f; digitized routing data 507g for defining how the fabricated dressing is to be routed to the patient (e.g., via an identified doctor and/or nurse) after fabrication and packaging is complete; and digitized application and/or removal information 507h for defining when and/or how the corresponding custom dressing (509) is to be applied to its corresponding wound and when and/or how the corresponding custom dressing (509) is to be removed from corresponding wound.

It is to be understood that the digitized patient identifying and wound identifying data 507f may be used multiple times including for associating the digitized wound image 507c with the actual wound, for associating the automatically fabricated dressing 509 with the actual wound; and for printing out or otherwise generating routing data 507g that causes the packaged product to be correctly ultimately routed to the same actual wound 580'. In one embodiment, the digitized patient identifying and wound identifying data 507f and the digitized routing data 507g are formed as computer data files at substantially the same time and in substantially the same location as the digitized wound map or image 507c is created (and generally by a same person for all three files) so that the wound map or image 507c is correctly attached or otherwise logically associated with and tied to the patient identifying and wound identifying data 507f and to the routing data 507g from the point of inception of the wound image. This minimizes the risk that a wrong dressing will be applied to a wrong wound or even a wrong patient or not properly or timely delivered to the patient due to accidental mix up of one or more of these pieces of functional information.

The digitized wound characterizing maps and/or plots 507d and corresponding treatment plans (which could be digitized text notes appended to the wound zone characterizing maps) are typically generated by a doctor or other skilled health care providing professional(s) at the same time (and/or same place) that the digitized application and/or removal information 507h is generated so that the two files (507d, 507h) correctly correlate with one another. The latter two files (507d, 507h) are then appended to or otherwise logically connected to at least the digitized patient identifying and wound identifying data 507f and the digitized routing data 507g. In one embodiment, the digitized wound characterizing maps and/or plots 507d delineate skin zones and/or other zones that are to be protected from exposure to exudates or other tissue harming substances by use of one or more fluid containment barriers such as for example those made with embedded viscous silicones or the like. In one embodiment, the digitized wound identifying data 507f includes data identifying and locating on the identified patient, a frame of reference (e.g., corresponding to X/Y frames shown in FIG. 5B) relative to which the wound dressing is to be oriented and identifying the prescribed orientation of the dressing. The digitized routing data 507g may include an audit trail that identifies the doctor(s) or other skilled health care providing professional(s) who characterized the wound zones and the adjacent skin areas that may need protection, and who created the treatment plan. The routing data 507g may also identify the doctor(s), nurse(s) or other skilled health care professional(s) who are delegated the task of aligned-wise applying the wound dressing to the identified wound and/or removing the wound dressing from the identified wound at the treatment prescribed appropriate times. This minimizes the risk that a wrong dressing will be designed, fabricated and applied to a wrong wound or even a wrong patient or not properly or timely delivered to the patient or not properly removed from the wound due to accidental mix up of one or more of these pieces of functional information regarding routing and responsibility for data management and for use of the associated custom wound dressing or the packaged product that includes the custom wound dressing. Since in one embodiment the responsible people are so-identified by a file kept in a database and logically associated with the identified patient and identified wound, a game of finger pointing cannot be later played so as to escape responsibility regarding who had the responsibility to make sure the right custom dressing is correctly applied to the correspondingly matching wound at the appropriate time and thereafter removed at an appropriate time.

The digitized dressing design maps 507e can be generated in automated response to the digitized wound characterizing maps and/or plots 507d and corresponding treatment plans or they may be generated by a skilled dressing designer with automated assistance provided by a computer (e.g., 507) that suggests to the dressing designer what shapes, sizes and materials should be picked for each dressing layer, how many dressing layers should be used for each treatment function and how vertical and/or horizontal fluid containment barriers (e.g., 543a, 543b, 545, 531b, 572) should be shaped, dimensioned, located and formed of respective fluid containing materials in or between the various dressing layers. It is therefore understood that the digitized dressing design maps 507e can include specifications for the shapes, dimensions, locations and/or fluid containing materials to be used for forming respective vertical and/or horizontal fluid containment barriers (e.g., 543a, 543b, 545, 531b, 572) within or on the surfaces of the various dressing layers. In one embodiment, the digitized dressing design maps 507e include specifications for the shape, dimensions, locations and/or barrier forming materials to be used for protecting adjacent skin from harmful substances such as is done for example by lower barrier 545 of FIG. 5A. The digitized dressing design maps 507e may further include information regarding amounts, locations, and identities of one or more prespecified liquids (e.g., water, saline solution, peroxide, antiseptics, etc.) that are to be applied to prespecified liquid containment areas of the customized wound dressing after removal from the package 206/207/208 but prior to application of the dressing to a corresponding wound.

It is also to be understood that the digitized dressing design maps 507e may be appended to otherwise logically associated (e.g., in a relational database) with one or more of the other data files 507c-507d, 507f-507h and that the digitized dressing design maps 507e may be used for controlling automated fabrication (592) of the corresponding wound dressing 509. Identification of the person or persons respectively responsible for generating the digitized dressing design maps 507e and for responsively fabricating the corresponding wound dressing 509 may be appended into the digitized routing data file 507g at the times of respective dressing design and dressing fabrication. The unique identification number (e.g., Rx number, not shown) that is optionally included on label 204 may be submitted, in one embodiment, to a relational database (e.g., one implemented in computer 507) after the wound dressing is fabricated and all of files 507c-507h contained therein may be responsively retrieved for review and evaluation. The relational database may include additional files or records that logically tie to the unique dressing identification number (e.g., Rx number, not shown) and that indicate how well the patient responded to the automatically designed and automatically fabricated custom wound dressing 509 and/or to medicines or other substances added thereinto.

The present disclosure is to be taken as illustrative rather than as limiting the scope, nature, or spirit of the subject matter claimed below. Numerous modifications and variations will become apparent to those skilled in the art after studying the disclosure, including use of equivalent functional and/or structural substitutes for elements described herein, use of equivalent functional couplings for couplings described herein, and/or use of equivalent functional steps for steps described herein. Such insubstantial variations are to be considered within the scope of what is contemplated here. Moreover, if plural examples are given for specific means, or steps, and extrapolation between and/or beyond such given examples is obvious in view of the present disclosure, then the disclosure is to be deemed as effectively disclosing and thus covering at least such extrapolations.

By way of example, it is understood that the configuring of a coordinating computer (e.g., 507 of FIG. 5B) in accordance with the disclosure can include formulation of algorithms that take advantage of the ability to form custom patterned vertical and/or horizontal barriers for one or more layers of a multi-layer custom dressing. As such, machine executable instructing signals may be stored in a functional storage of a computer to determine one or more barrier defining parameters including but not limited to: which of plural barrier forming liquids to use, where to deposit the selected barrier forming liquids and to what depth; what order to deposit the selected barrier forming liquids in; what temperature to heat the deposited barrier forming liquids to if at all; what overlying or underlying horizontal barriers to form adjacent to the vertical barriers; and so forth. A computer-readable medium (e.g., 507b) or another form of a data storage product (including but not limited to, a hard disk, a compact disk, a flash memory unit, a downloading of manufactured instructing signals over a network and/or the like may be manufactured and used for defining one or more data structures for custom fabricating a wound dressing for a corresponding individual wound where the data structures include one or more of a wound zones map, a wound zones characterizing map, layer by layer dressing design maps, patient and wound identification data, dressing routing data and dressing usage data; where the data structures are logically linked to one another to thereby verify that not only a correct custom dressing is automatically fabricated for a given wound, but that the fabricated dressing is thereafter timely routed to the corresponding wound.

Reservation of Extra-Patent Rights, Resolution of Conflicts, and Interpretation of Terms After this disclosure is lawfully published, the owner of the present patent application has no objection to the reproduction by others of textual and graphic materials contained herein provided such reproduction is for the limited purpose of understanding the present disclosure of invention and of thereby promoting the useful arts and sciences. The owner does not however disclaim any other rights that may be lawfully associated with the disclosed materials, including but not limited to, copyrights in any computer program listings or art works or other works provided herein, and to trademark or trade dress rights that may be associated with coined terms or art works provided herein and to other otherwise-protectable subject matter included herein or otherwise derivable herefrom.

If any disclosures are incorporated herein by reference and such incorporated disclosures conflict in part or whole with the present disclosure, then to the extent of conflict, and/or broader disclosure, and/or broader definition of terms, the present disclosure controls. If such incorporated disclosures conflict in part or whole with one another, then to the extent of conflict, the later-dated disclosure controls.

Unless expressly stated otherwise herein, ordinary terms have their corresponding ordinary meanings within the respective contexts of their presentations, and ordinary terms of art have their corresponding regular meanings within the relevant technical arts and within the respective contexts of their presentations herein. Descriptions above regarding related technologies are not admissions that the technologies or possible relations between them were appreciated by artisans of ordinary skill in the areas of endeavor to which the present disclosure most closely pertains.

Given the above disclosure of general concepts and specific embodiments, the scope of protection sought is to be defined by the claims appended hereto. The issued claims are not to be taken as limiting Applicant's right to claim disclosed, but not yet literally claimed subject matter by way of one or more further applications including those filed pursuant to 35 U.S.C. §120 and/or 35 U.S.C. §251.

What is claimed is:

1. A custom wound dressing comprising:
   (a) a plurality of layers extending laterally in the dressing, the plurality of layers including a wound interfacing layer that is configured to interface with a specific wound, the wound interfacing layer having a porous hydrophilic material; and
   (b) at least one barrier in the wound interfacing layer for preventing or inhibiting a liquid absorbed by the porous hydrophilic material from spreading laterally from one side of the barrier to an opposed other side of the barrier.

2. The custom wound dressing of claim 1 wherein the barrier essentially consists of a silicone or a silicone oil.

3. The custom wound dressing of claim 2 wherein said silicone or silicone oil has a viscosity in the range of about 1 CentiStoke to about 10,000 cSt.

4. The custom wound dressing of claim 1 wherein said silicone or silicone oil has a viscosity in the range of about 100 cSt to about 1000 cSt.

5. The custom wound dressing of claim 1 wherein the barrier substantially prevents a liquid that is harmful to skin from migrating through or out of the wound interfacing layer to contact a skin area adjacent to the wound interfacing layer.

6. The custom wound dressing of claim 4 wherein wound interfacing layer is dimensioned to contact at least one pre-mapped adjacent skin zone and the barrier is positioned to align over the at least one pre-mapped adjacent skin zone.

7. The custom wound dressing of claim 6 wherein the pre-mapped adjacent skin zone surrounds the wound and the barrier is positioned to cover the entirety of the pre-mapped adjacent skin zone.

8. The custom wound dressing of claim 1 wherein the at least one barrier extends from the wound interfacing layer to an adjacent layer of the plurality of layers.

9. The custom wound dressing of claim 1 wherein the adjacent layer comprises hydrophobic material.

10. A combination of a package and a custom wound dressing enclosed in the package wherein the wound dressing comprises:
    (a) a plurality of layers extending laterally in the dressing, including a layer of porous hydrophilic material; and
    (b) at least one barrier embedded in the layer of porous hydrophilic material, the barrier configured to prevent or inhibit a first liquid absorbed by the layer of the hydrophilic material from spreading laterally from one side of the barrier to an opposite side of the barrier, where the barrier is positioned at a location corresponding to a location of at least one of pre-mapped skin zones.

11. The combination of claim 10 wherein the barrier includes a substantial amount of a silicone or a silicone oil for causing the barrier to have hydrophobic properties.

12. The combination of claim 10 wherein the barrier includes a mineral oil or a vegetable oil.

13. The combination of claim 10 wherein the barrier includes a water repelling liquid having a viscosity in the range of about 1 CentiStoke to about 10,000 cSt.

14. The combination of claim 10 wherein the layer of porous hydrophilic material is configured to interface with an identified wound.

15. The combination of claim 14 wherein the barrier includes a coloring dye.

16. The combination of claim 14 wherein the barrier is positioned to align over the at least one pre-mapped adjacent skin zone and to protect the adjacent skin zone from exposure to harmful substances.

17. The combination of claim 10 wherein the barrier is positioned to protectively align relative to the at least one pre-mapped adjacent skin zone and to protect the adjacent skin zone from exposure to harmful substances.

18. The combination of claim 10 wherein said plurality of laterally extending layers include a gas or vapor permeable porous and hydrophobic layer that is permeable in at least one zone of the second layer by a predefined gas or vapor.

19. The combination of claim 18 wherein the gas or vapor permeable porous and hydrophobic layer has one or more custom patterned zones of comparatively reduced or essentially no permeability for the predefined gas or vapor in addition to having said at least one zone exhibiting comparatively larger permeability to the predefined gas or vapor and wherein the one or more custom patterned zones correspond to zones of an identified wound.

20. The combination of claim 19 wherein a first of the custom patterned zones with reduced or essentially no permeability is positioned above the barrier.

21. The combination of claim 19 wherein the gas or vapor permeable porous and hydrophobic layer contains intersecting nonwoven microfibers and said one or more custom patterned zones of comparatively reduced or essentially no permeability include corresponding films formed by melting of the microfibers.

22. The combination of claim 19 wherein the gas or vapor permeable porous and hydrophobic layer contains intersecting nonwoven microfibers and said one or more custom patterned zones of comparatively reduced or essentially no permeability include a laterally extending gas impermeable film deposited on the microfibers.

23. The combination of claim 19 wherein the gas or vapor permeable porous and hydrophobic layer contains intersecting nonwoven microfibers having an average pore size less than less than about 0.5 micron.

24. The combination of claim 10 and further comprising:
    (c) within said plurality of laterally extending layers, another layer of porous hydrophilic material; and
    (d) at least another barrier embedded in the other layer of porous hydrophilic material for preventing or inhibiting liquid absorbed by the other layer of hydrophilic material from spreading laterally from one side of the other barrier to an opposed other side of the other barrier.

25. The combination of claim 24 and further comprising:
    (e) between the first and second laterally extending hydrophilic layers, one or more laterally extending fluid barriers that are impermeable to a predefined liquid and/or impermeable to a predefined vapor or gas, and where there is at least one zone between the first and second laterally extending hydrophilic layers where the predefined liquid, predefined vapor or gas can flow between the laterally extending hydrophilic layers.

26. The combination of claim 10 wherein said package comprises:
    (c) a first packaging sheet;
    (d) a second packaging sheet, attached to the first sheet; and (e) at least a first label integrally formed on or attached to one of said first and second packaging sheets and providing said indicia that identifies the specific wound.

27. The combination of claim 26 wherein the first said indicia includes a graphic or schematic of at least one of body anterior and body posterior and an indication of where on the represented body anterior or body posterior the identified wound is located.

28. The combination of claim 26 wherein the at least first label further provides second indicia separately identifying the patient having the identified wound.

29. The combination of claim 26 wherein the at least first label further provides second indicia indicating a route and/or method by way of which said combination of the package and the custom dressing are to be delivered to the identified wound or patient having an identified wound.

30. The combination of claim 26 wherein the at least first label further provides second indicia indicating at least one of a prescribed date for application or prescribed date for removal of the dressing respectively to or from an identified wound.

31. The combination of claim 26 wherein the at least first label further provides second indicia defining or pointing to instructions for applying or removing the dressing respectively to or from an identified wound.

32. The combination of claim 31 wherein said second indicia points to a computer network site that provides instructions for applying or removing the dressing respectively to or from an identified wound.

33. The combination of claim 26 wherein the first packaging sheet includes a thermally printable-on layer and the at least first label is integrally formed as thermal printing on said thermally printable-on layer.

34. The combination of claim 26 and further comprising:
(f) a second label integrally formed on or attached to one of said first and second packaging sheets and providing additional indicia that performs at least one of the following functions:
   indicating a route or method by way of which said combination of the package and the custom dressing are to be delivered to a patient,
   indicating at least one of a prescribed date for application or prescribed date for removal of the dressing respectively to or from the identified wound, and
   defining or pointing to instructions for applying or removing the dressing respectively to or from the identified wound.

35. The combination of claim 26 further comprising an adhesive ring that sealing bonds the first and second packaging sheets to one another.

36. The combination of claim 10 wherein the at least one barrier extends from the wound interfacing layer to an adjacent layer of the plurality of layers.

37. The combination of claim 36 wherein the adjacent layer comprises hydrophobic material.

* * * * *